US 11,844,534 B2

(12) United States Patent
Bhatia et al.

(10) Patent No.: US 11,844,534 B2
(45) Date of Patent: Dec. 19, 2023

(54) ARTICULATING ROTARY CUTTING TOOL

(71) Applicant: Joint Preservation Innovations, LLC, Naperville, IL (US)

(72) Inventors: Sanjeev Bhatia, Naperville, IL (US); Peter J. Millett, Edwards, CO (US); James Orrico, Evanston, IL (US)

(73) Assignee: JOINT PRESERVATION INNOVATIONS, LLC, Naperville, IL (US)

( * ) Notice: Subject to any disclaimer, the term of this patent is extended or adjusted under 35 U.S.C. 154(b) by 71 days.

(21) Appl. No.: 17/582,476

(22) Filed: Jan. 24, 2022

(65) Prior Publication Data
US 2023/0190308 A1    Jun. 22, 2023

Related U.S. Application Data

(63) Continuation of application No. PCT/US2021/064168, filed on Dec. 17, 2021.

(51) Int. Cl.
*A61B 17/16* (2006.01)

(52) U.S. Cl.
CPC ...... *A61B 17/1617* (2013.01); *A61B 17/1631* (2013.01); *A61B 17/1633* (2013.01); *A61B 17/1642* (2013.01); *A61B 17/1666* (2013.01); *A61B 17/1684* (2013.01); *A61B 2017/1602* (2013.01)

(58) Field of Classification Search
CPC ............ A61B 17/1631; A61B 17/1617; A61B 17/1633; A61B 17/1615; A61B 17/1624; A61B 2017/1602
See application file for complete search history.

(56) References Cited

U.S. PATENT DOCUMENTS

| 5,464,407 A * | 11/1995 | McGuire ................ B25G 1/043 |
| | | 606/86 R |
| 5,916,146 A | 6/1999 | Allotta et al. |
| 7,118,574 B2 | 10/2006 | Patel et al. |
| 7,682,307 B2 | 3/2010 | Danitz et al. |

(Continued)

FOREIGN PATENT DOCUMENTS

WO    2021/219258 A1    11/2021

OTHER PUBLICATIONS

International Search Report and Written Opinion issued for corresponding International Application No. PCT/US2021/064168 dated Mar. 11, 2022.

*Primary Examiner* — Amy R Sipp
(74) *Attorney, Agent, or Firm* — Morgan, Lewis & Bockius LLP

(57) ABSTRACT

A rotary cutting tool including an elongated housing having a proximal end and a distal end, the elongated housing extends circumferentially around a first axis. A drive shaft disposed within the elongated housing and extending between the proximal end and the distal end and rotatable about the first axis. A cutting bit housing coupled to the distal end of the elongated housing and rotatable relative to the drive shaft about an articulation axis between a non-articulated position and one or more articulated positions. A rotary cutting bit coupled to the cutting bit housing and the drive shaft and rotatable about the articulation axis with the cutting bit housing, the rotary cutting bit and drive shaft forming a constant velocity joint.

29 Claims, 15 Drawing Sheets

(56) References Cited

U.S. PATENT DOCUMENTS

| | | |
|---|---|---|
| 7,785,252 B2 | 8/2010 | Danitz et al. |
| 7,862,554 B2 | 1/2011 | Hegeman et al. |
| 8,277,375 B2 | 10/2012 | Danitz et al. |
| 2005/0165420 A1 | 7/2005 | Cha |
| 2005/0261692 A1* | 11/2005 | Carrison ............ A61B 17/1631 606/79 |
| 2007/0083081 A1 | 4/2007 | Schlagenhauf et al. |
| 2009/0023988 A1* | 1/2009 | Korner ............... A61B 17/1633 600/114 |
| 2009/0171359 A1 | 7/2009 | Sterrett |
| 2009/0177202 A1* | 7/2009 | May ................. A61B 17/32002 606/79 |
| 2010/0057087 A1* | 3/2010 | Cha .................... A61B 17/1633 606/80 |
| 2010/0179557 A1* | 7/2010 | Husted ............ A61B 17/32002 600/300 |
| 2010/0217269 A1 | 8/2010 | Landes |
| 2011/0022078 A1 | 1/2011 | Hinman |
| 2013/0211408 A1* | 8/2013 | Kather ............... A61B 17/1604 606/83 |
| 2014/0058394 A1* | 2/2014 | Siegal ................ A61B 17/1631 606/80 |
| 2016/0302876 A1 | 10/2016 | Teichtmann |
| 2019/0059910 A1* | 2/2019 | Adams ............... A61B 17/1617 |
| 2021/0128174 A1 | 5/2021 | Cannon |
| 2021/0298768 A1 | 9/2021 | Biton et al. |
| 2022/0096099 A1 | 3/2022 | Bhatia et al. |
| 2022/0096110 A1 | 3/2022 | Bhatia et al. |

\* cited by examiner

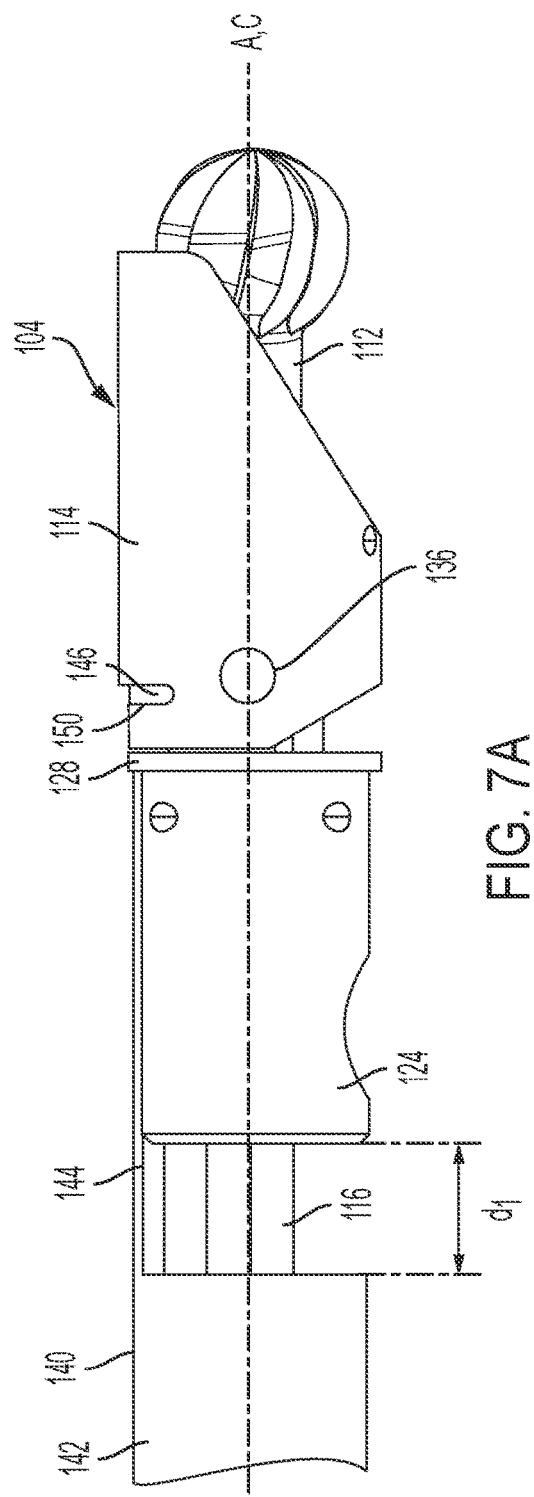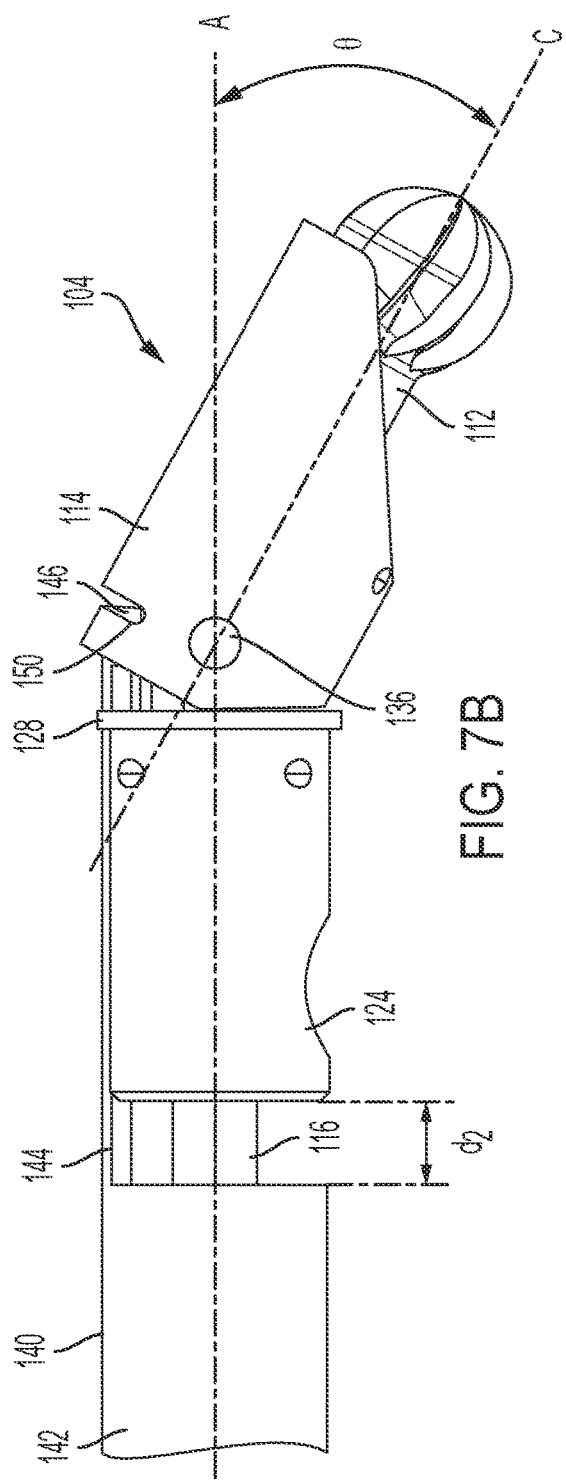
FIG. 7A
FIG. 7B

ARTICULATING ROTARY CUTTING TOOL

CROSS REFERENCE TO RELATED APPLICATIONS

This application is a Continuation of International Patent Application No. PCT/US2021/064168 filed Dec. 17, 2021, which is hereby incorporated by reference in its entirety for all purposes.

FIELD OF THE INVENTION

The present invention generally relates to surgical cutting tools and, more particularly, to a surgical rotary cutting tool having an articulable head.

BACKGROUND

Bone spurs typically develop in human joints, the spinal column and skulls and can frequently be a source of pain from impingement or nerve compression. The spurs may also cause loss of joint motion and degenerative wear of the affected joints or adjacent tissues. In situations where surgical intervention is required, these bone spurs are typically removed under direct arthroscopic or endoscopic visualization using conventional rotary cutting tools, such as arthroscopic or open surgical burrs that may be either straight or angled in a fixed position. The fixed position of said burrs often limits the reach of conventional surgical burrs. As such, it is often difficult or nearly impossible to use these types of burrs to remove bone spurs arthroscopically, endoscopically, open, or robotically especially from hard-to-reach areas, in tight spaces, or when working through a cannula. Additionally, the curvature of the bone on which the bone spur exists makes reaching the bone spur, during surgery, difficult or even impossible with conventional arthroscopic or open surgical burrs due to their fixed positions.

Conventional arthroscopic or open surgical burrs often have low stability, wear or degrade quickly, and/or produce excess vibration and noise during use, which negatively impacts their use during surgical procedures such as, but not limited to, arthroscopic surgery, endoscopic spinal surgery, open surgery, and robotic surgical applications. Arthroscopic burrs include cutting or drilling heads and are designed to be rotatably driven to cause the cutting or drilling head to rotate about an axis thereby allowing the cutting or drilling head to shave away or remove the bone spur. The rotational speed of the cutting or drilling head has a direct impact on the ability of the arthroscopic burr to effectively shave away or remove said bone spur. As such, during arthroscopic surgery, a certain rotational speed or range of rotational speeds may be desired, in order to ensure the safety and effectiveness of the surgery. In conventional arthroscopic burrs, the rotational speed of the drilling head is negatively impacted when the drilling head is articulated, such that the use of said burr is limited at the desired rotational speeds. Additionally, the size of arthroscopic burrs is relatively small due to the anatomic constraints and due to their use in minimally invasive surgeries. As such, the difficulty of manufacturing the components of said burrs is increased due to their relatively small size.

Therefore, there exists a need in the art for a rotary cutting or drilling tool for use in arthroscopic, endoscopic, open, and robotic surgeries that has an articulable cutting or drilling head that can reliably operate at a constant desired rotational speed when articulated. Furthermore, there exists a need in the art for a rotary cutting or drilling tool that also has high stability, will not degrade, or wear quickly, that does not produce excess vibration and/or noise, and that can be easily manufactured.

SUMMARY

In one embodiment, there is a rotary cutting tool including an elongated housing having a proximal end and a distal end, the elongated housing extending circumferentially around a first axis. The rotary cutting tool further includes a drive shaft disposed within the elongated housing and extending between the proximal end and the distal end and rotatable about the first axis. The rotary cutting tool further includes a cutting bit housing coupled to the distal end of the elongated housing and rotatable relative to the drive shaft about an articulation axis between a non-articulated position and one or more articulated positions. The rotary cutting tool further includes a rotary cutting bit including a multi-faceted ball, the rotary cutting bit coupled to the cutting bit housing and the drive shaft and rotatable about the articulation axis with the cutting bit housing, the multi-faceted ball of the rotary cutting bit and drive shaft forming a constant velocity joint.

In some embodiments, the rotary cutting tool further includes a controller assembly coupled to the proximal end of the elongated housing and configured to cause the rotary cutting bit and cutting bit housing to selectively rotate relative to the elongated housing between the non-articulated position and the one or more articulated positions. In some embodiments, the rotary cutting tool further includes an articulation shaft disposed between the elongated housing and the drive shaft and including an engagement member configured to engage with a groove in the cutting bit housing. The controller assembly may be coupled to the articulation shaft and configured to cause the articulation shaft to translate relative to the elongated housing and translation of the articulation shaft relative to the elongated housing may cause the rotary cutting bit and cutting bit housing to rotate relative to the elongated housing about an articulation axis.

In some embodiments, the controller assembly includes a first trigger and a second trigger, the second trigger configured to cause the articulation shaft to translate relative to the elongated housing and the first trigger configured to releasably lock a position of the articulation shaft relative to the elongated housing. In some embodiments, the first trigger includes an arm configured to abut a stepped structure of the second trigger such that the rotation of the second trigger in at least one direction is prevented by the arm of the first trigger. In some embodiments, the stepped structure includes one or more stepped surfaces that each correspond to a different articulated position of the one or more articulated positions. In some embodiments, the articulation shaft and engagement member are coupled to one another by an elongated arm integrally formed with the articulation shaft and engagement member, the articulation shaft, engagement member and elongated arm comprised of a generally rigid material.

In some embodiments, the drive shaft includes a rotary socket configured to receive the multi-faceted ball of the rotary cutting bit, the multi-faceted ball and rotary socket forming the constant velocity joint. In some embodiments, the rotary socket is rotatably fixed to the drive shaft such that rotation of the drive shaft about the first axis causes the rotary socket to rotate about the first axis, the rotary socket defines a receiving area for receiving the multi-faceted ball, and the receiving area has a generally hexagonal shape and the multi-faceted ball is a hex-ball. In some embodiments, the rotary socket includes a groove extending circumferentially around the rotary socket, and the elongated housing is configured to receive two fasteners such that the two fasteners are at least partially received within the groove to prevent translation of the rotary socket about the first axis.

In some embodiments, the rotary cutting tool further includes a connecting member coupled to the distal end of the elongated housing, the connecting member rotatably defining the articulation axis and connecting the cutting bit housing to the elongated housing. In some embodiments, the cutting bit housing is snap-fit to the connecting member. In some embodiments, the rotary cutting bit includes a groove extending circumferentially around a central shaft of the rotary cutting bit, the groove configured to receive a fastener to prevent the rotary cutting bit from translating relative to an intended cutting axis.

In another embodiment, there is an arthroscopic rotary cutting tool including an elongated housing having a proximal end and a distal end, the elongated housing extending circumferentially around a first axis, and a drive shaft disposed within the elongated housing and extending between the proximal end and the distal end and rotatable about the first axis. The arthroscopic rotary cutting tool further includes a cutting bit housing coupled to the distal end of the elongated housing and rotatable relative to the drive shaft about an articulation axis between a non-articulated position and one or more articulated positions and a rotary cutting bit including a multi-faceted ball, the rotary cutting bit coupled to the cutting bit housing and the drive shaft and rotatable about the articulation axis with the cutting bit housing, the multi-faceted ball of the rotary cutting bit and drive shaft forming a constant velocity joint. The arthroscopic rotary cutting tool further includes a controller assembly coupled to the proximal end of the elongated housing and configured to cause the rotary cutting bit and cutting bit housing to selectively rotate relative to the elongated housing between the non-articulated position and the one or more articulated positions and an articulation shaft disposed between the elongated housing and the drive shaft and including an engagement member configured to engage with a groove in the cutting bit housing. The controller assembly is coupled to the articulation shaft and configured to cause the articulation shaft to translate relative to the elongated housing and translation of the articulation shaft relative to the elongated housing causes the rotary cutting bit and cutting bit housing to rotate relative to the elongated housing about an articulation axis.

In some embodiments, the controller assembly includes a first trigger and a second trigger, the second trigger configured to cause the articulation shaft to translate relative to the elongated housing and the first trigger configured to releasably lock a position of the articulation shaft relative to the elongated housing. In some embodiments, the first trigger includes an arm configured to abut a stepped structure of the second trigger such that the rotation of the second trigger in at least one direction is prevented by the arm of the first trigger. In some embodiments, the stepped structure includes one or more stepped surfaces that each correspond to a different articulated position of the one or more articulated positions. In some embodiments, the drive shaft includes a rotary socket configured to receive the multi-faceted ball of the rotary cutting bit, the multi-faceted ball and rotary socket forming the constant velocity joint.

In some embodiments, the rotary socket is rotatably fixed to the drive shaft such that rotation of the drive shaft about the first axis causes the rotary socket to rotate about the first axis, the rotary socket defines a receiving area for receiving the multi-faceted ball, and the receiving area has a generally hexagonal shape and the multi-faceted ball is a hex-ball. In some embodiments, the rotary socket includes a groove extending circumferentially around the rotary socket, and the elongated housing is configured to receive two fasteners such that the two fasteners are at least partially received within the groove to prevent translation of the rotary socket about the first axis. In some embodiments, the arthroscopic rotary cutting tool further includes a connecting member coupled to the distal end of the elongated housing, the connecting member rotatably defining the articulation axis and connecting the cutting bit housing to the elongated housing.

In another embodiments, there is a rotary cutting bit including a cutting head, a central shaft coupled to the cutting head, the central shaft defining a groove extending circumferentially around the central shaft, and a multi-faceted ball coupled to the central shaft opposite the cutting head, the multi-faceted ball including one or more faceted surfaces being generally curved in an axial direction and being generally flat in along the outer edge of each cross section taken perpendicular to the axial direction.

BRIEF DESCRIPTION OF THE DRAWINGS

The foregoing summary, as well as the following detailed description of embodiments of the articulating rotary cutting tool, will be better understood when read in conjunction with the appended drawings of an exemplary embodiment. It should be understood, however, that the invention is not limited to the precise arrangements and instrumentalities shown.

In the drawings:

FIG. 7A is a close-up, side elevational view of the distal end of the articulating rotary cutting tool of FIG. 1 with the elongated housing removed and the articulating head assembly in the non-articulated position;

FIG. 7B is a close-up, side elevational view of the distal end of the articulating rotary cutting tool of FIG. 1 with the elongated housing removed and the articulating head assembly in an articulated position;

DETAILED DESCRIPTION

Figure 1:
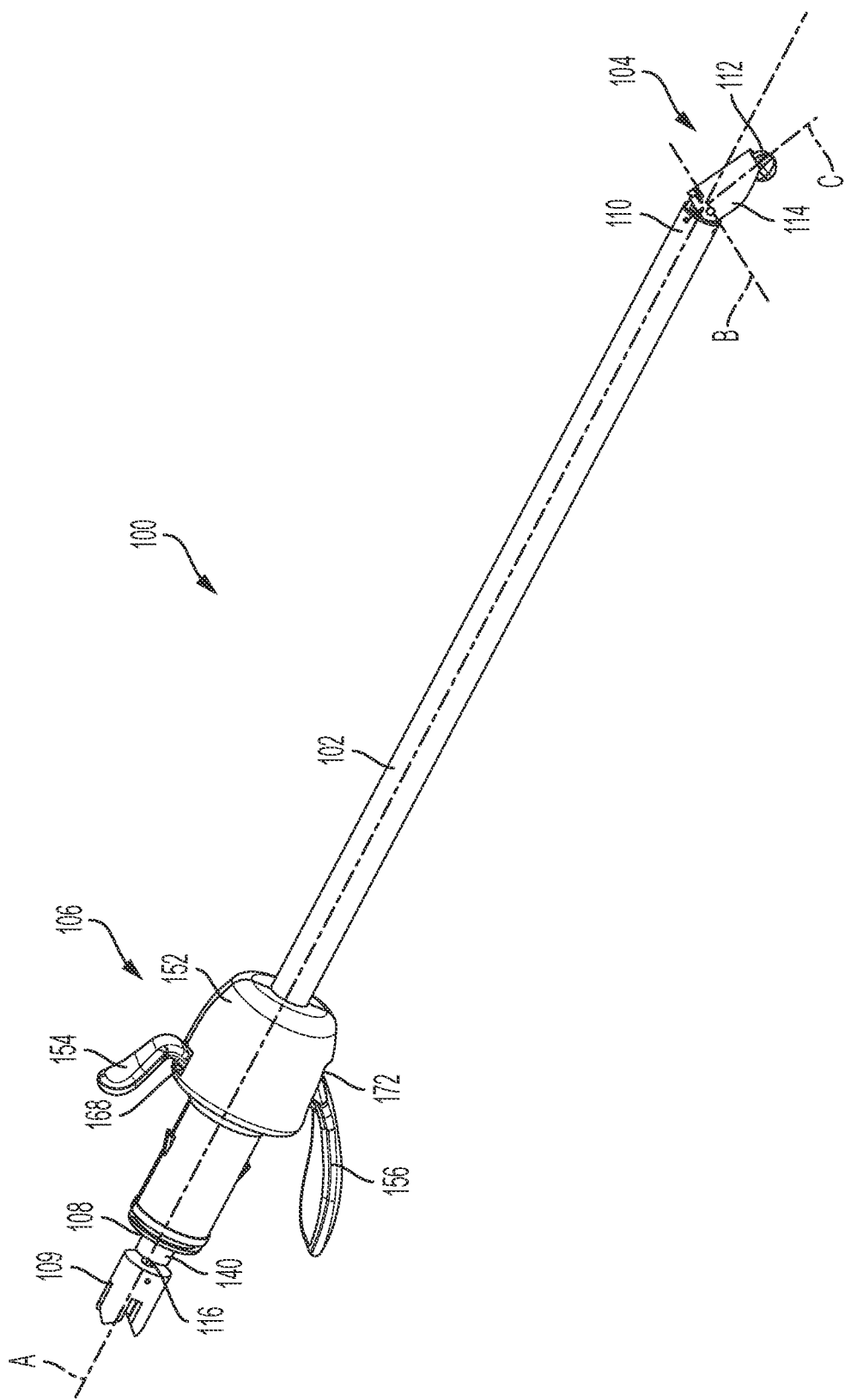
FIG. 1 is a perspective view of an articulating rotary cutting tool in accordance with an exemplary embodiment of the present disclosure.

Referring to the drawings in detail, wherein like reference numerals indicate like elements throughout, there is shown in FIGS. 1-13 an articulating rotary cutting tool, generally designated 100, in accordance with an exemplary embodiment of the present invention.

Referring to FIG. 1, the articulating rotary cutting tool 100 may include an elongated housing 102, an articulating head assembly 104, and a controller assembly 106. The articulating head assembly 104 may include a cutting and/or drilling means (e.g., a rotary cutting bit 112) that is articulable to allow the articulating rotary cutting tool 100 to resect (e.g., drill, shave, or cut) at one or more desired angles, as discussed in more detail below. The controller assembly 106 may be configured to selectively control the articulation of the articulating head assembly 104 between articulated positions and a non-articulated position, as discussed in more detail below. In some embodiments, the articulating rotary cutting tool 100 may be an arthroscopic articulating rotary tool configured to be used in arthroscopic procedures. For example, the articulating rotary cutting tool 100 may be configured to be used in arthroscopic procedures that involve the removal of bone spurs from a body. The articulating head assembly 104 may be configured to effectively cut, drill or shave away said bone spurs from the body. In some embodiments, the articulating rotary cutting tool 100 may be configured to be used in a robotic surgical environment. For example, the articulating rotary cutting tool 100 may be configured to be used by a robotic device for performing an arthroscopic surgery.

The articulating head assembly 104 and/or the controller assembly 106 may be coupled to the elongated housing 102. For example, the controller assembly 106 and articulating head assembly 104 may each be coupled to the elongated housing 102 at different positions. The controller assembly 106 may be coupled to a proximal end 108 of the elongated housing 102. The articulating head assembly 104 may be coupled to a distal end 110 of the elongated housing 102 opposite the proximal end 108. The elongated housing 102 may extend along a first axis A. In some embodiments, the elongated housing 102 extends circumferentially around the first axis A such that the elongated housing 102 has a generally circular cross-sectional shape. The elongated housing 102 may be hollow such that one or more components may be positioned within the elongated housing 102, as discussed in more detail below. In some embodiments, the elongated housing 102 is comprised of a metal, metal alloy, plastic material, and/or a composite material. In some embodiments, the elongated housing 102 is comprised of stainless steel (e.g., 316 stainless steel).

Figure 12:
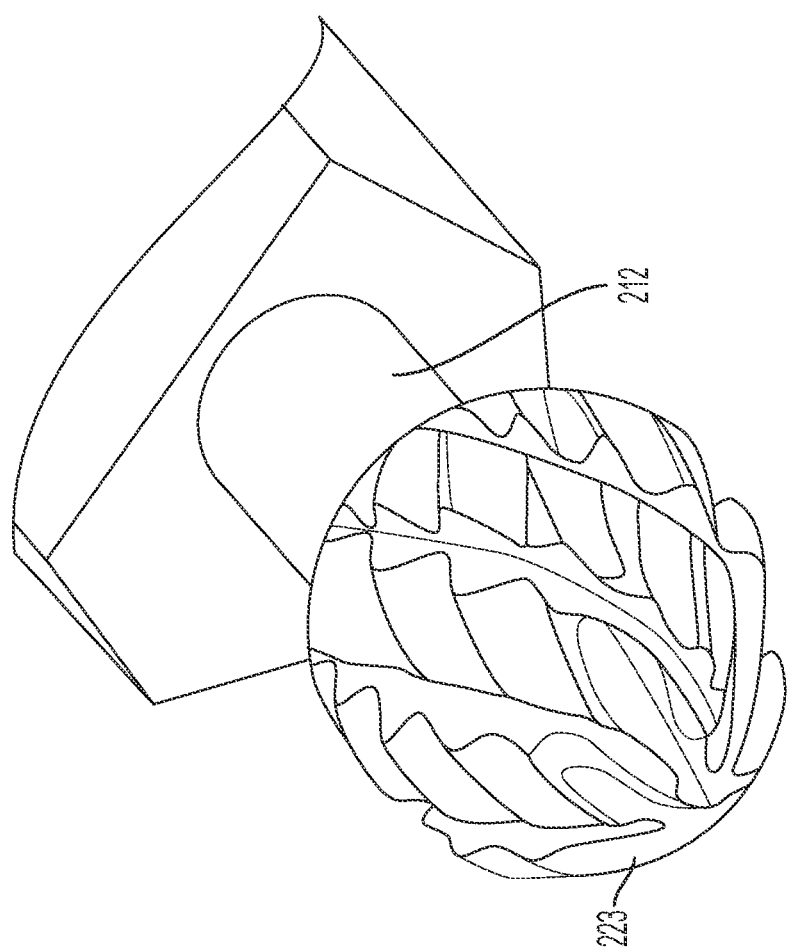
FIG. 12 is a perspective view of another rotary cutting bit that may be coupled to the articulating rotary cutting tool of FIG. 1.

The articulating head assembly 104 may include a rotary cutting bit 112 configured to resect a desired surface (e.g., tissue, bone or cartilage) when the rotary cutting bit 112 is rotated about a cutting axis C, at a desired rotational velocity. The rotary cutting bit 112 may include a cutting head 123 defining one or more surfaces (e.g., flutes) for resecting. In some embodiments, the cutting head 123 is integrally formed with the rotary cutting bit 112. It will be understood that although a single type of cutting head 123 is shown in the figures, any type of cutting head (e.g., a cutting head with a different flute pattern) may be used. For example, as shown in FIG. 12 there is a rotary cutting bit 212 that is generally the same as rotary cutting bit 112 except that it includes a cutting head 223 having a double cut burr pattern. The rotary cutting bit 212 may be interchangeable with the rotary cutting bit 112 and may function in generally the same manner as the rotary cutting bit 112. In some embodiments, the rotary cutting bit 112 is comprised of a metal, metal alloy, plastic material, and/or composite material. In some embodiments, the rotary cutting bit 112 is comprised of a combination of carbide and carbon steel. Referring back to FIG. 1, the articulating head assembly 104 may include a cutting bit housing 114 at least partially covering the rotary cutting bit 112. The cutting bit housing 114 may act as a guard or sheath to the rotary cutting bit 112 such that portions of the rotary cutting bit 112 are prevented from contacting unwanted surfaces and/or to block debris during use. The rotary cutting bit 112 and/or the cutting bit housing 114 may be rotatably coupled to the elongated housing 102 such that each is rotatable about an articulation axis B. For example, the rotary cutting bit 112 and/or the cutting bit housing 114 may articulate about the articulation axis B between one or more articulated positions and a non-articulated position. Articulation of the articulating head assembly 104 may refer to the rotation of the rotary cutting bit 112 about the articulation axis B. In some embodiments, the cutting bit housing 114 is comprised of a metal, metal alloy, plastic material, and/or composite material. In some embodiments, the cutting bit housing 114 is comprised of polyetheretherketone ("PEEK"). In other embodiments, the cutting bit housing 114 is comprised of a stainless steel.

In some embodiments, the rotary cutting bit 112 and cutting bit housing 114 are fixedly coupled to one another with respect to rotation about the articulation axis B. For example, the rotary cutting bit 112 and cutting bit housing 114 may be coupled such that rotation of the cutting bit housing 114 about the articulation axis B in a direction causes the rotary cutting bit 112 to rotate about the articulation axis B in the same direction. In some embodiments, the rotary cutting bit 112 is rotatably coupled to the cutting bit housing 114 with respect to rotation about the cutting axis C. For example, the rotary cutting bit 112 may rotate about the cutting axis C while the cutting bit housing 114 remains fixed relative to the cutting axis C. In this manner, the articulating head assembly 104 may be rotated about the articulation axis B between different positions and the rotary cutting bit 112 may be rotated about the cutting axis C for cutting and/or drilling.

Figure 2:
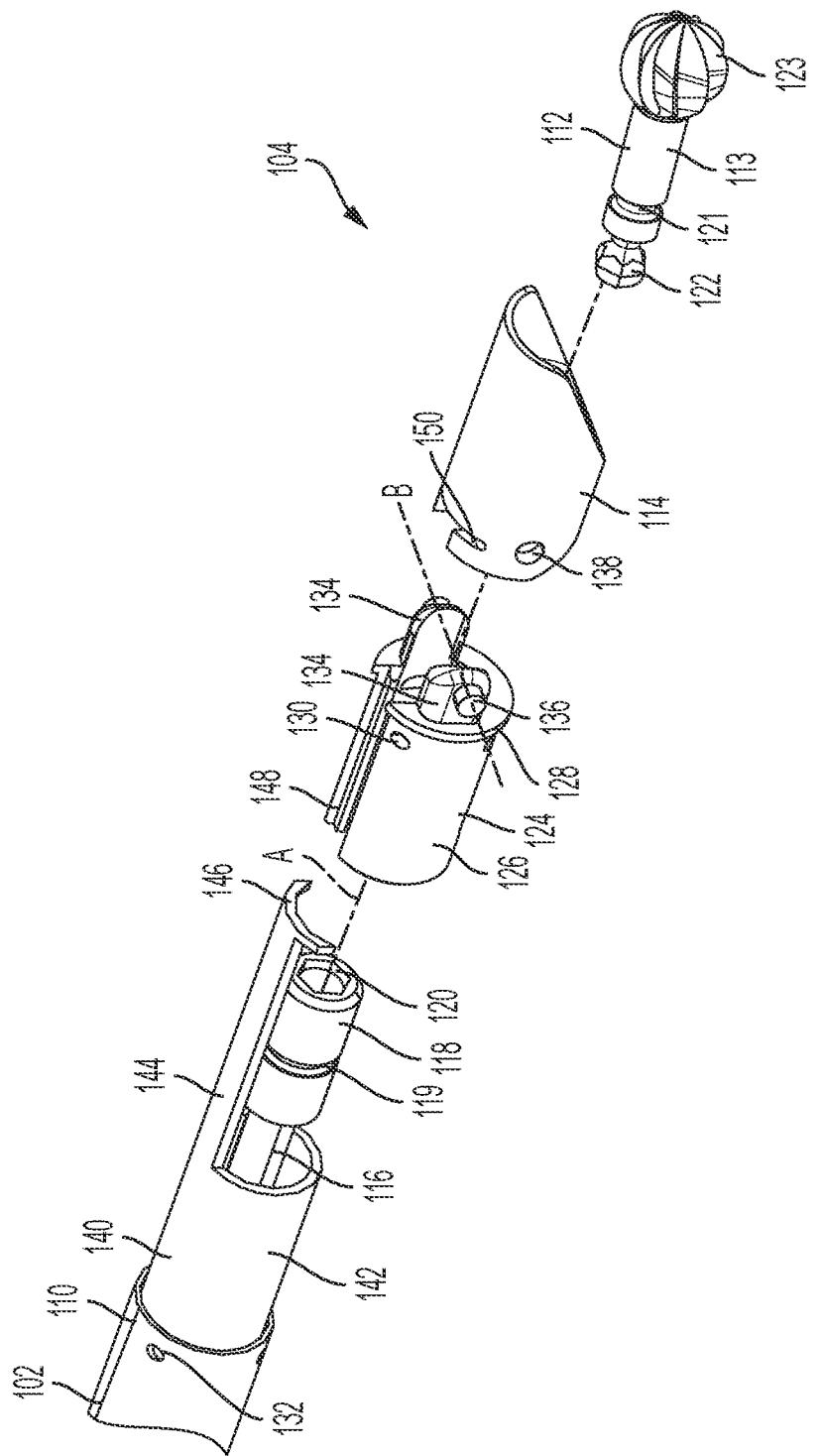
FIG. 2 is a partially exploded view of a distal end of the articulating rotary cutting tool shown in FIG. 1.

Referring to FIGS. 1-2, the articulating rotary cutting tool 100 may include a drive shaft 116 configured to rotate the rotary cutting bit 112 about the cutting axis C. The drive shaft 116 may extend along the first axis A and be positioned at least partially within the elongated housing 102. For example, a portion of the drive shaft 116 extends outwardly from the proximal end 108 of the elongated housing 102 along the first axis A as shown in FIG. 1. The remaining portion of the drive shaft 116 extends along the first axis A from the proximal end 108 to the distal end 110 of the elongated housing 102. What is shown in FIG. 2 is a partially exploded view of the distal end 110 of the elongated housing 102 and the articulating head assembly 104 and it will be understood that when assembled, the drive shaft 116 may not extend beyond the distal end 110 of the elongated housing 102. The drive shaft 116 may extend circumferentially around the first axis A and have a diameter that is less than the elongated housing 102 to allow the drive shaft 116 to be positioned within the elongated housing 102. In some embodiments, the drive shaft 116 is comprised of a metal, metal alloy, plastic, and/or composite material. In some embodiments, the drive shaft 116 is comprised of a stainless steel (e.g., 304 stainless steel).

The drive shaft 116 may be configured to translate rotational motion from an external drive means (e.g., a motor) to the rotary cutting bit 112 such that the rotary cutting bit 112 is rotatably driven about the cutting axis C. In some embodiments, the drive shaft 116 is rotatable about the first axis A such that rotation of the drive shaft 116 about the first axis A causes the rotary cutting bit 112 to rotate about the cutting axis C. In some embodiments, there is a drive interface 109 fixedly coupled to the drive shaft 116 and configured to couple the external drive means to the articulating rotary cutting tool 100. The drive interface 109 may be rotatably fixed to the drive shaft 116 such that rotation of the drive interface 109 causes the drive shaft 116 to be rotated. In this manner, the drive shaft 116 may translate rotational motion from the external drive means, via the drive interface 109, to the rotary cutting bit 112. In some embodiments, the drive interface 109 may be detachably coupled to the drive shaft 116 such that a different drive interface may be coupled to the drive shaft 116. In some embodiments, the drive interface 109 is comprised of a metal, metal alloy, plastic material, and/or composite material. In some embodiments, the drive interface 109 is comprised of a synthetic polymer (e.g., Nylon 6/6, Nylon 12). In some embodiments, the drive interface 109 is comprised of a stainless steel.

The rotary cutting bit 112 may be rotatably coupled to the drive shaft 116 by a rotary socket 118. The rotary socket 118 may be fixedly coupled to the drive shaft 116 such that the rotary socket 118 rotates with the drive shaft 116. The rotary socket 118 may include a receiving area 120 configured to couple the rotary cutting bit 112 to the rotary socket 118. The receiving area 120 may define one or more generally flat inner surfaces 120i configured to engage with a corresponding faceted surface of the rotary cutting bit 112 to allow the rotary cutting bit 112 to be rotated about the articulation axis B without disengaging from the receiving area 120. In some embodiments, the rotary cutting bit 112 includes a multi-faceted ball 122 disposed at a proximal end of the rotary cutting bit 112. The multi-faceted ball 122 defines one or more faceted surfaces configured to engage the inner surfaces 120i of the receiving area 120. In some embodiments, the number of faceted surfaces on the multi-faceted ball 122 and the number of inner surfaces 120i of the receiving area 120 correspond to one another. For example, the multi-faceted ball 122 may be a hex-ball having a generally hexagonal cross-sectional shape and the receiving area 120 may define six inner surfaces 120i forming a generally hexagonal shape. In this manner, one or more faceted surfaces of the multi-faceted ball 122 may engage the inner surfaces 120i of the receiving areas 120. As such, the multi-faceted ball 122, when received within the receiving area 120, is rotatably fixed to the rotary socket 118 about the first axis A and/or the cutting axis C while being rotatable about the articulation axis B. In this manner, the multi-faceted ball 122 is rotatably coupled to the drive shaft 116, by the rotary socket 118, such that rotation of the drive shaft 116 causes the rotary cutting bit 112 to rotate. In some embodiments, the rotary socket 118 is comprised of a metal, metal alloy, plastic material, and/or composite material. In some embodiments, the rotary socket 118 is comprised of a stainless steel (e.g., 440 stainless steel).

Figure 3A:
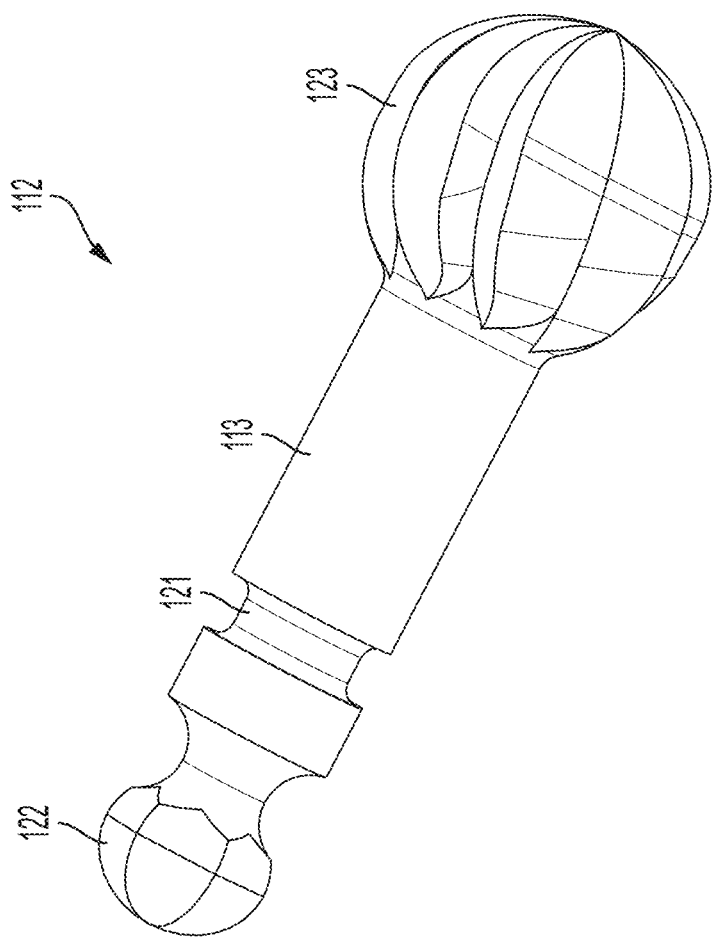
FIG. 3A is a side perspective view of the rotary cutting bit of FIG. 1.
Figure 3B:
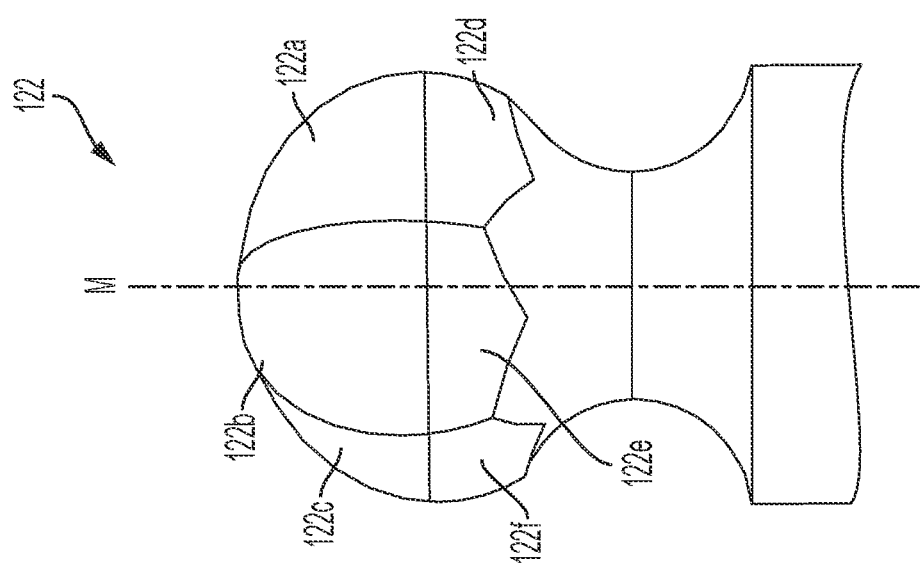
FIG. 3B is a close-up, side elevational view of the multi-faceted ball of the rotary cutting bit of FIG. 1.
Figure 3C:
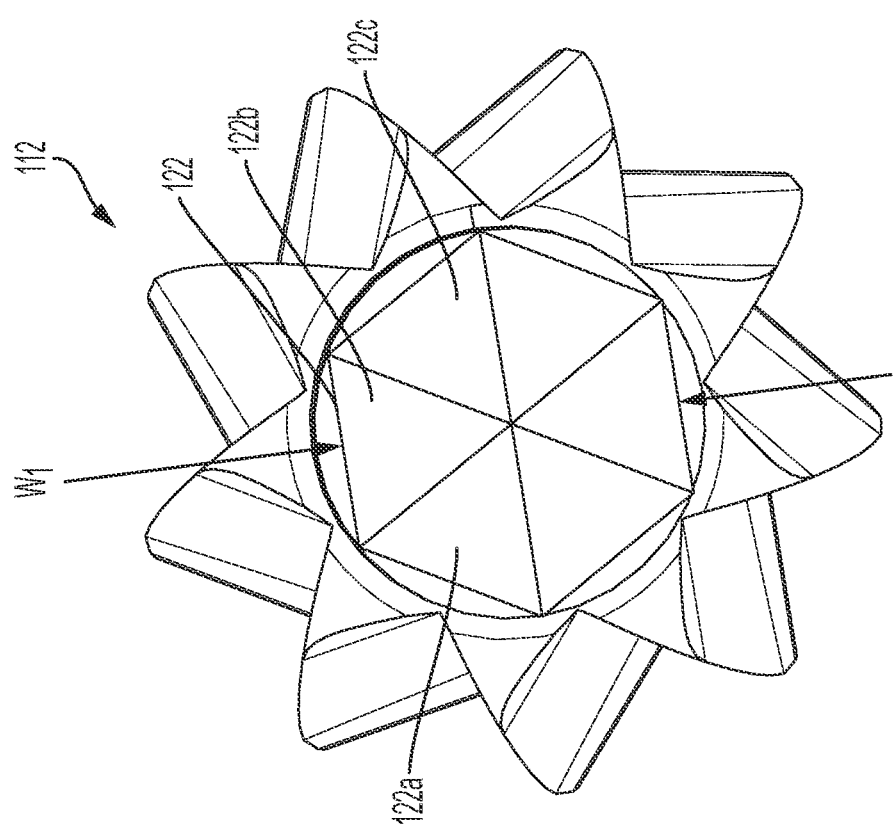
FIG. 3C is a rear elevational view of the rotary cutting bit of FIG. 1.

The multi-faceted ball 122 may be better understood with reference to FIGS. 3A-3C. As shown in FIG. 3B, the multi-faceted ball 122 may include faceted surfaces 122a-122f. In FIG. 3B, the multi-faceted ball 122 is shown from a top elevational view and it will be understood that the opposite side of the multi-faceted ball 122 may include surfaces generally the same as faceted surfaces 122a-122f on the opposite side in generally the same configuration. In some embodiments, the faceted surfaces 122a-122f are curved in an axial direction M and generally flat in along the outer edge of each cross section taken perpendicular to the axial direction M. For example, each faceted surface 122a-122f is curved in an axial direction as best shown in FIG. 3B. In some embodiments, each faceted surface 122a-122f may have a corresponding radius of curvature measured from the axial axis M to the outer edge of each faceted surface 122a-122f.

In some embodiments, each of the faceted surfaces 122a-122c may have generally the same radius of curvature and each of the faceted surfaces 122d-122f may have generally the same radius of curvature. In some embodiments, the radius of curvature of the faceted surfaces 122a-122c may be different than the radius of curvature of faceted surfaces 122d-122f. In other embodiments, the radius of curvature may be generally the same for each of the multi-faceted surfaces 122a-122f. As such, the curved aspect of the faceted surfaces 122a-122f may allow the multi-faceted ball 122 to rotate about the articulation axis B when disposed within the receiving area 120 and engaged with the corresponding inner surfaces 120i of the receiving area. As mentioned, the faceted surfaces 122a-122f may be generally flat in along the outer edge of each cross section taken perpendicular to the axial direction M as best shown in FIG. 3B. As such, the generally flat aspect of the faceted surfaces 122a-122f may engage the inner surfaces 120i of the receiving area 120 such that the multi-faceted ball 122 is rotatably fixed to the rotary socket 118 with respect to rotation about the first axis A and/or the cutting axis C. In some embodiments, the faceted surfaces 122a-122f may be machined to have a smooth finish. In some embodiments, during machining, the faceted surfaces 122a-122f may be lubricated to reduce build-up of excess heat and thereby reduce unintended warping of the faceted surfaces 122a-122f during machining. In some embodiments, the faceted surfaces 122a-122f may be coated with a material and/or composite material to increase the lubricity of the faceted surfaces 122a-122f.

Figure 4:
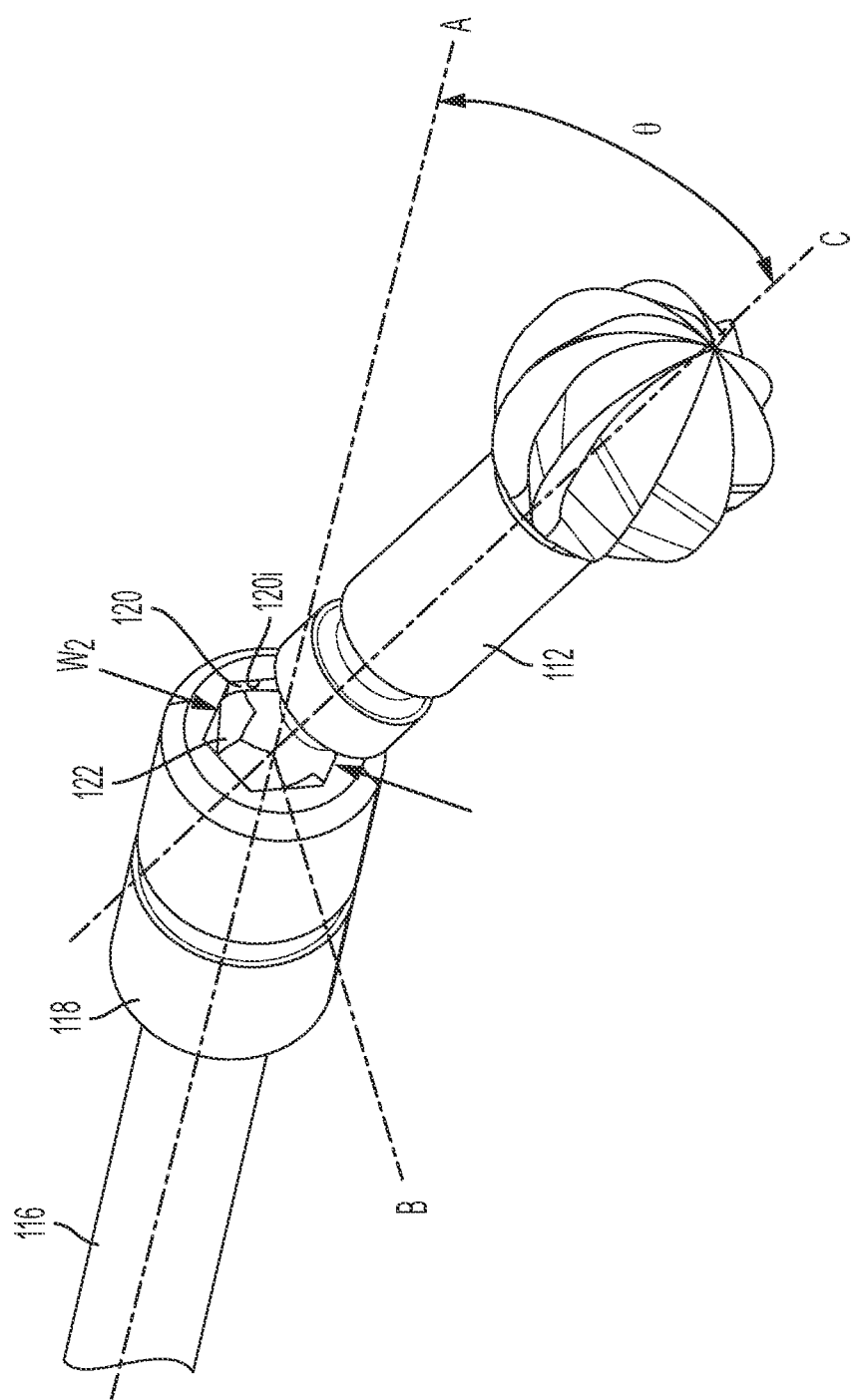
FIG. 4 is a close-up perspective view of the distal end of the articulating rotary cutting tool of FIG. 1 where the rotary cutting bit is in an articulated position.

Referring to FIGS. 3C and 4, in some embodiments, the multi-faceted ball 122 has a width $W_1$ as measured in a direction perpendicular to two opposing side edges of the multi-faceted ball 122. The side edges may refer to the edges of the multi-faceted ball 122 where the upper multi-faceted surfaces 122a-122c and lower multi-faceted surfaces meet. Put another way the side edges of the multi-faceted ball form the periphery of the hexagonal shape shown in FIG. 3C. In some embodiments, the receiving area 120 has a width $W_2$ as measured in a direction perpendicular to two opposing side surfaces of the receiving area 120. For example, the width $W_2$ may be measured between two opposing inner surfaces 120i of the receiving area 120. In some embodiments, the width $W_1$ of the multi-faceted ball 122 is generally equal to the width $W_2$ of the receiving area 120. In some embodiments the width $W_1$ of the multi-faceted ball 122 is slightly less than the width $W_2$ of the receiving area 120. For example, the width $W_1$ of the multi-faceted ball 122 may be between about 0.091 inches and about 0.092 inches. The width $W_2$ of the receiving area 120 may be between about 0.093 inches and about 0.096 inches.

Referring to FIG. 4, in some embodiments, the drive shaft 116 and rotary cutting bit 112 form a constant velocity joint such that the drive shaft 116 may transmit power to the rotary cutting bit 112, regardless of the angle of the rotary cutting bit 112, at a constant rotational speed. Put another way, the rotational speed of the drive shaft 116 may be generally equal to the rotational speed of the rotary cutting bit 112, regardless of the angle of the rotary cutting bit 112. For example, the rotary cutting bit 112 is shown in an articulated position where the cutting axis C is offset from the first axis A at an angle θ. In some embodiments, the angle θ may be between about 0 degrees to about 30 degrees. The drive shaft 116 may rotate about the first axis A at a first rotational velocity, thereby causing the rotary socket 118 to rotate about the first axis at the same rotational velocity. As the rotary socket 118 rotates at the first rotational velocity, the receiving area 120 rotates at the same velocity as well. The engagement of the inner surfaces of the receiving area 120 with the multi-faceted ball 122 causes the multi-faceted ball 122, and therefore the rotary cutting bit 112, to rotate about the cutting axis C at a second rotational velocity, where the second rotational velocity is generally equal to the first rotational velocity.

Figure 5:
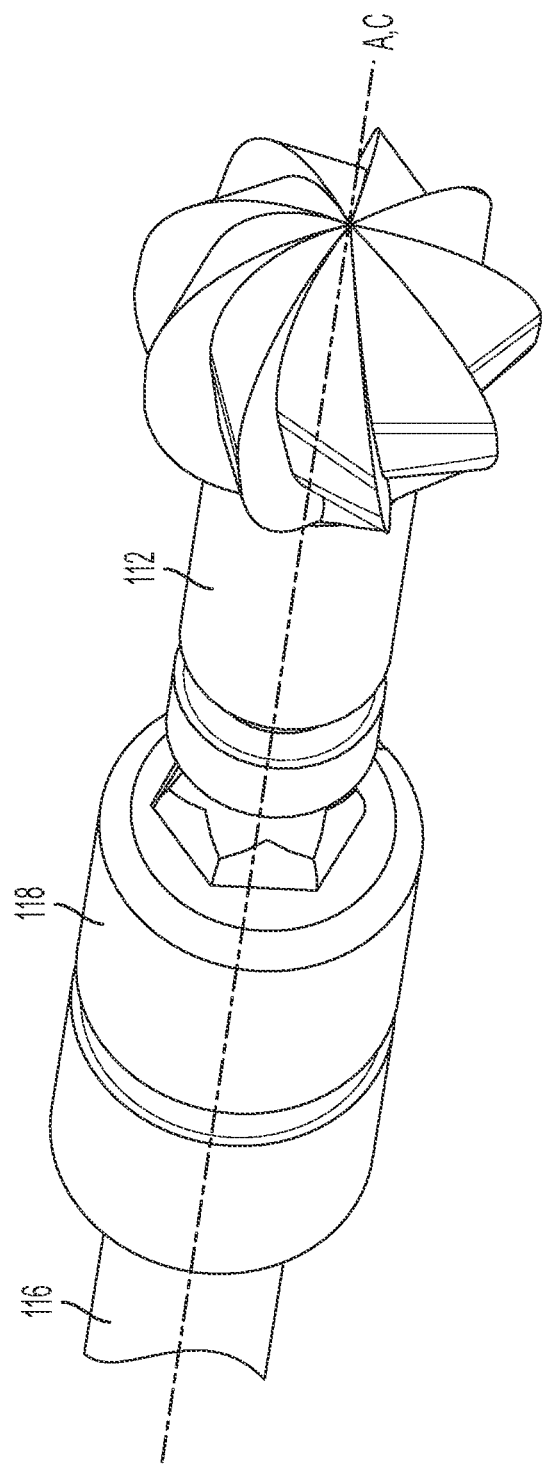
FIG. 5 is a close-up perspective view of the distal end of the articulating rotary cutting tool of FIG. 1 where the rotary cutting bit is in a non-articulated position.

Although the rotary cutting bit 112 is shown at an offset angle to the drive shaft 116 in FIG. 4, it will be understood that the rotational velocity of the rotary cutting bit 112 may be generally the same as the drive shaft 116 when the rotary cutting bit 112 and drive shaft 116 are aligned. For example, as shown in FIG. 5, the rotary cutting bit 112 is shown aligned with the drive shaft 116 (e.g., in a non-articulated position). In the non-articulated position, the cutting axis C and first axis A may be aligned such that the cutting axis C is not offset from the first axis A. Put another way, the cutting axis C is parallel to and positioned along the first axis A, or vice versa. As such, the drive shaft 116, rotary socket 118, and rotary cutting bit 112 may rotate about the first axis A and/or the cutting axis C, at generally the same velocity, when the rotary cutting bit 112 is in the non-articulated position.

By forming a constant velocity joint between the drive shaft 116 and rotary cutting bit 112 (e.g., via the rotary socket 118 and multi-faceted ball 122), the articulating rotary cutting tool 100 may be capable of cutting and/or drilling at a consistent desired speed, regardless of the angle of the rotary cutting bit 112. For example, in minimally invasive surgeries safe operation of the articulating rotary cutting tool 100 requires that a minimum rotational speed of the rotary cutting bit 112 be maintained. By providing the constant velocity joint, as discussed above, the rotary cutting bit 112 may be consistently rotationally driven by the drive shaft 116 at a desired rotational velocity regardless of the angle of the rotary cutting bit 112.

In FIG. 4, there is a single constant velocity joint formed between the multi-faceted ball 122 and the rotary socket 118 to allow the rotary cutting bit 112 to be rotatably driven at a constant velocity when the rotary cutting bit 112 is at an angle θ of up to 30 degrees. However, it will be understood that one or more additional constant velocity joints (e.g., two or more total constant velocity joints) may be provided in series such that the rotary cutting bit 112 may be rotatably driven about the cutting axis C at an angle θ that is greater than 30 degrees. For example, another rotary socket (not shown) may be provided that includes a receiving area, generally the same as receiving area 120, and a multi-faceted ball, generally the same as the multi-faceted ball 122, positioned on the end of the additional rotary socket opposite the receiving area. The multifaceted ball of the additional rotary socket may be received within receiving area 120 of the rotary socket 118 such that a first constant velocity joint is formed between the rotary socket 118 and the additional rotary socket. Furthermore, the multi-faceted ball 122 of the rotary cutting bit 112 may be received within the receiving area of the additional rotary socket, generally the same as how the multi-faceted ball 122 is received within receiving area 120 of rotary socket 118 to form a second constant velocity joint. In this manner, the additional rotary socket may rotate relative to the rotary socket 118 and the rotary cutting bit 112 may rotate relative to the additional rotary socket such that a greater angle θ of articulation may be achieved. For example, by providing an additional constant velocity joint, the articulating head assembly 104 may be capable of being rotated up to 35 degrees, 40 degrees, or 45 degrees.

As such, each constant velocity joint may be used in series to selectively rotate the rotary cutting bit 112. The constant velocity joints being coupled to one another in series as discussed above may be characterized as distal and proximal constant velocity joints where the distal constant velocity joint is the joint formed from the multi-faceted ball that is integrally formed with the rotary cutting bit 112. Similarly, the proximal constant velocity joint would be the joint formed from the multi-faceted ball that is directly coupled to the rotary socket 118. The proximal and distal constant velocity joints may be independently rotated relative to the first axis A such that different articulation angles may be achieved. For example, the proximal constant velocity joint may be rotated relative to the rotary socket 118 while the distal constant velocity joint remains aligned with the proximal constant velocity joint to achieve a first articulation angle of the rotary cutting bit 112. As such, the distal constant velocity joint may be rotated relative the proximal constant velocity joint to achieve a second articulation angle of the rotary cutting bit 112 that is greater than the first articulation angle. It will be understood, however, that the distal constant velocity joint may be rotated relative to the proximal constant velocity joint to achieve the first articulation angle while the proximal constant velocity joint remains aligned with the rotary socket 118.

As mentioned above, the articulating head assembly 104 may be selectively rotated, relative to the elongated housing 102, to allow a user (e.g., a doctor, surgeon, robotic surgical device) to adjustably select the angle at which cutting and/or drilling occurs. Referring back to FIG. 2, there may be a connecting member 124 coupled to the distal end 110 of the elongated housing 102 and configured to rotatably couple the articulating head assembly 104 to the elongated housing 102. The connecting member 124 may include a main body 126 configured to be positioned within the elongated housing 102 and a lip 128, fixedly coupled to the main body 126 and configured to abut against the distal end 110 of the elongated housing 102. For example, the main body 126 of the connecting member 124 may have a diameter what is less than the diameter of the inner surface of the elongated housing 102 to allow the main body 126 to be disposed within the elongated housing 102. The lip 128 may protrude from the main body 126 such that abuts the distal end 110 of the elongated housing 102, thereby preventing the main body 126 from being displaced toward the proximal end 108 of the elongated housing 102. In some embodiments, the connecting member 124 is comprised of a metal, metal alloy, plastic material, and/or composite material. In some embodiments, the connecting member 124 is comprised of polyetheretherketone. In some embodiments, the connecting member 124 is comprised of a stainless steel.

In some embodiments, the connecting member 124 is configured to create a seal to prevent fluid, tissue, and/or other debris from contacting the constant velocity joint formed between the multi-faceted ball 122 and the rotary socket 118. For example, the connecting member 124 may be configured to prevent fluid, tissue, and/or other debris from entering into the elongated housing 102 through the opening at the distal end 110 of the elongated housing that the connecting member 124 is positioned within. In some embodiments, the receiving area 120 of the rotary socket 118 may also prevent fluid, tissue, and/or other debris from contacting the portions of the multi-faceted ball 122 engaged with the inner surface 120i of the receiving area. For example, the receiving area 120 encapsulates portions of the multi-faceted ball 122, thereby preventing fluid, tissue, and/or debris from contacting those portions of the multi-faceted ball 122. In this manner, the connecting member 124 and/or the rotary socket 118 may prevent unintended dislodgement or disengagement of the rotary cutting bit 112 from the rotary socket 118 that may be caused by fluid, tissue, and/or debris entering into the constant velocity joined formed between the two.

Figure 13:
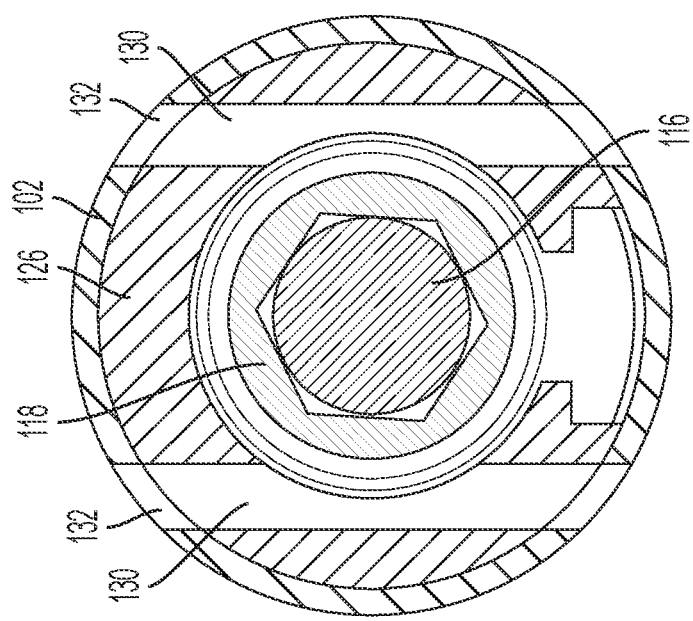
FIG. 13 is a front cross-sectional view of the distal end of the articulating rotary cutting tool of FIG. 1.

Still referring to FIG. 2, in some embodiments, the main body 126 is configured to receive one or more fasteners (e.g., pins, screws, bolts) to fixedly couple the main body 126 to the elongated housing 102. For example, the main body 126 may include one or more apertures 130 configured to align with one or more corresponding apertures 132 in the elongated housing 102 when the lip 128 abuts the distal end 110 of the elongated housing 102. When the apertures 130 and 132 are aligned, a pin may be inserted through each of the apertures 132 in the elongated housing 102 and extend through the apertures 130 on the main body 126 of the connecting member 124. For example, as shown in FIG. 13 the apertures 132 and 130 are aligned with one another such that a pin may be inserted through apertures 132 and extend through apertures 130 to fixedly couple the main body 126 to the elongated housing 102. Referring back to FIG. 2, the pins, when inserted, may abut the sidewalls of the apertures 130, 132 thereby preventing movement of the connecting member 124 relative to the elongated housing 102. In this manner, the connecting member 124 may be translationally and rotationally fixed relative to the elongated housing 102. Although not shown, the pins may be sized and/or shaped such that they do not protrude outwardly from the elongated housing 102. Put another way, the pins may be sized and/or shaped such that they are flush with an outer surface of the elongated housing 102 when the pins are received within the apertures 130 and 132. In some embodiments, the elongated housing 102 includes two apertures 132 proximate the distal end 110 of the elongated housing 102 and positioned opposite one another. Similarly, the main body 126 of the connecting member 124 may include two apertures 130. In some embodiments, at least one of apertures 130 and apertures 132 may have a generally circular cross sectional shape or may be an elongated slit.

In some embodiments, the rotary socket 118 may be translationally fixed relative to the elongated housing 102. For example, the rotary socket 118 may remain fixed relative the elongated housing 102 and may be rotated about the first axis A. The rotary socket 118 may include a recessed groove 119 extending circumferentially around the rotary socket 118. When assembled, the recessed groove 119 may align with the apertures 130, 132 such that the pin(s), used to fixedly couple the connecting member 124 to the elongated housing 102, may extend therethrough. The pins may be at least partially received within the recessed groove 119 such that the rotary socket 118 may be prevented from translating relative to the elongated housing 102 (e.g., translation along the first axis A). For example, the pins may be fixedly coupled to the elongated housing 102 and extend through the apertures 130, 132 and be at least partially recessed within the recessed groove 119. As such, the rotary socket 118 may rotate about the first axis A with little to no impediment from the pins but is prevented from translating in a direction, such as, but not limited to, along the first axis A, by the pins. In this manner, the position of the rotary socket 118 is fixed as the rotary socket 118 rotates about the first axis A, thereby preventing, or at least minimizing, unintended movement or jostling of the rotary cutting bit 112 as it is driven by the drive shaft 116.

As mentioned above, the connecting member 124 may be configured to rotatably couple the articulating head assembly 104 to the elongated housing 102. The connecting member 124 may include two arms 134 protruding from the lip 128 in a direction opposite the main body 126. Each of the arms 134 may include a protrusion 136 configured to couple the cutting bit housing 114 to the connecting member 124. In some embodiments, the protrusions 136 are integrally formed with the arms 134. The protrusions 136 may extend circumferentially around the articulation axis B such that the cutting bit housing 114, when coupled to the connecting member 124 via the protrusions 136, may rotate about the articulation axis B. For example, the cutting bit housing 114 may two apertures 138, one on each side of the cutting bit housing 114, configured to receive the protrusions 136 therein. In this manner, the cutting bit housing 114 may be rotatably coupled to the connecting member 124. In some embodiments, the arms 134 may be elastically deformable such that the cutting bit housing 114 may be snap-fit into engagement with the connecting member 124. For example, the arms 134 may elastically deform inwardly, toward one another, as the cutting bit housing 114 is slid over the arms 134 until the apertures 138 align with the protrusions 136 thereby allowing the arms 134 to return to their undeformed state (as shown in FIG. 2). In this manner, assembly of the connecting member 124 and cutting bit housing 114 may be easier than if the protrusions 136 were replaced with a detachable pin.

Figure 6:
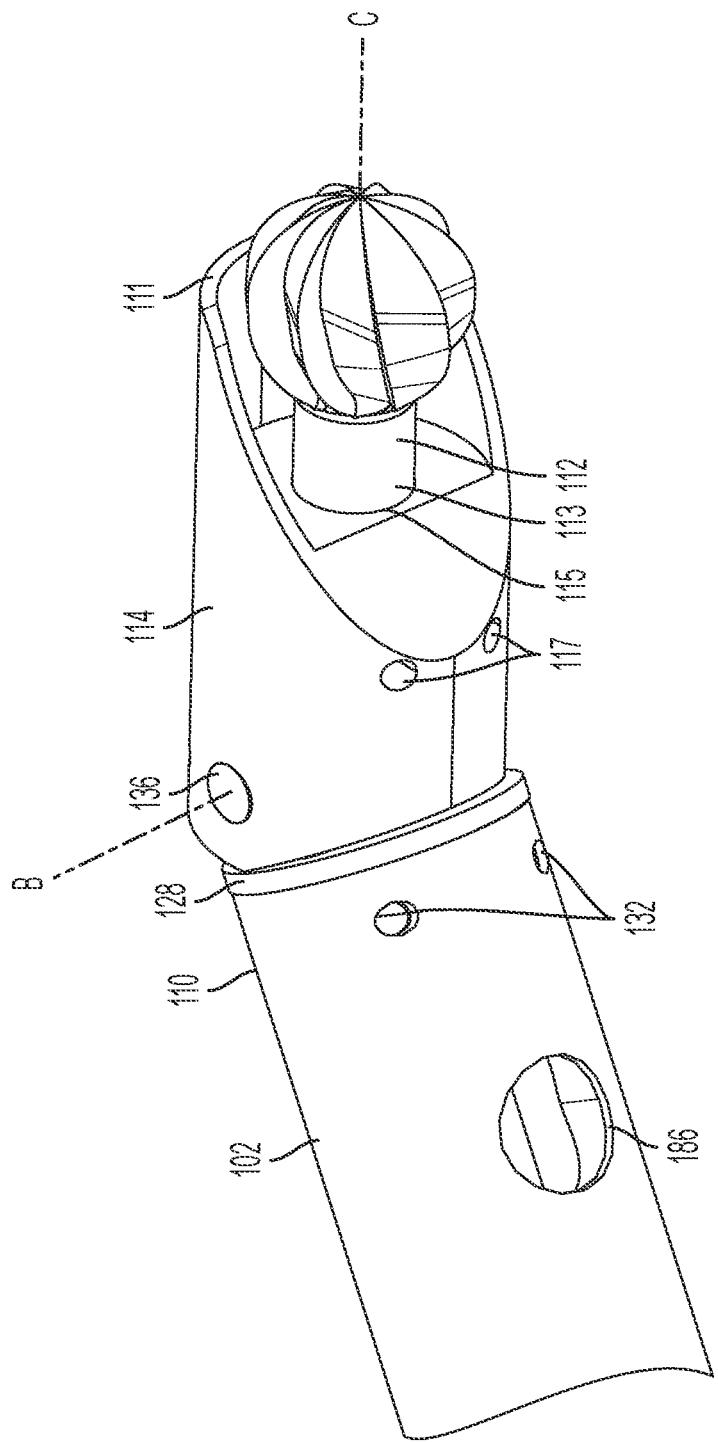
FIG. 6 is a close-up bottom perspective view of the distal end of the articulating rotary cutting tool of FIG. 1.

Referring to FIGS. 2 and 6, the cutting bit housing 114 may be configured to rotate the rotary cutting bit 112 about the articulation axis B. The cutting bit housing 114 may include an aperture 115 sized to receive at least a portion of the rotary cutting bit 112 such that the rotary cutting bit 112 may rotate about the articulation axis B with the cutting bit housing 114. For example, a central shaft 113 of the rotary cutting bit 112 extends through the aperture 115. In this manner, the rotary cutting bit 112 is rotationally fixed to the cutting bit housing 114 with respect to rotation about the articulation axis B while allowing the rotary cutting bit 112 to rotate relative to the cutting bit housing 114 about the cutting axis C. In some embodiments, the rotary cutting bit 112 is detachable from the cutting bit housing 114 and rotary socket 118 such that the rotary cutting bit 112 may be replaced with another rotary cutting bit similar to rotary cutting bit 112 or a different rotary cutting bit.

In some embodiments, the cutting bit housing 114 includes a shield 111 integrally formed with the cutting bit housing 114 and configured to at least partially cover the rotary cutting bit 112. The shield may act as a guard or sheath to the rotary cutting bit 112 such that portions of the rotary cutting bit 112 are prevented from contacting unwanted surfaces and/or to block debris during use. In some embodiments, the rotary cutting bit 112 may include a groove 121 extending circumferentially around the central shaft 113 and configured to prevent unintended translation of the rotary cutting bit 112 along the cutting axis C. For example, the cutting bit housing 114 defines two apertures 117 for receiving fasteners (e.g., screw, bolt, pin), not shown. The apertures 117 may be generally aligned with the groove 121 in the rotary cutting bit 112 when the rotary cutting bit 112 is engaged with the rotary socket 118 and extends through aperture 115. In this manner, the fasteners may extend through the apertures 117 and be at least partially positioned within the groove 121 such that the fasteners prevent the rotary cutting bit 112 from translating along the cutting axis C while allowing the rotary cutting bit 112 to rotate about the cutting axis C.

Referring back to FIG. 2, there may be an articulation shaft 140 positioned within the elongated housing 102 and configured to selectively rotate the articulating head assembly 104 about the articulation axis B. The articulation shaft 140 may include a main shaft 142, an elongated arm 144, and an engagement member 146. In some embodiments, the main shaft 142, elongated arm 144 and engagement member 146 are integrally formed. The main shaft 142 may be positioned between the drive shaft 116 and elongated housing 102. In some embodiments, the main shaft 142 extends substantially along the length of the elongated housing 102 between the proximal end 108 and distal end 110. The main shaft 142 may extend circumferentially around the first axis A. The elongated arm 144 may protrude from the main shaft 142 and couple the engagement member 146 to the main shaft 142. In some embodiments, the elongated arm 144 is sized to extend across the connecting member 124 such that a portion of the elongated arm 144 extends past the lip 128 of the connecting member 124. The connecting member 124 may define a track 148 positioned along a top surface of the connecting member 124 and sized to receive at least a portion of the elongated arm 144. In some embodiments, the articulation shaft 140 is comprised of a metal, metal alloy, plastic material, and/or a composite material. In some embodiments, the articulation shaft 140 is comprised of a stainless steel 9 (e.g., 316 stainless steel).

In some embodiments, the articulation shaft 140 is configured to translate relative to the elongated housing 102, in a direction parallel to the first axis A, to cause the articulating head assembly 104 to rotate about the articulation axis B. For example, the engagement member 146 may be configured to engage the cutting bit housing 114 to selectively articulate the cutting bit housing 114 about the articulation axis B. The cutting bit housing 114 may include a groove 150 positioned along a top surface of the cutting bit housing 114 and configured to receive the engagement member 146. As such, when the articulation shaft 140 is translated in a direction parallel to the first axis A, the engagement member 146 also translates in the same direction. As such, the engagement of the groove 150 in the cutting bit housing 114 with the engagement member 146 may cause the cutting bit housing 114 to rotate about the articulation axis B, when the engagement member 146 is translated relative to the elongated housing 102. As discussed above, rotation of the cutting bit housing 114 may be rotationally fixed to the rotary cutting bit 112 with regards to rotation about the articulation axis B. In this manner, translation of the articulation shaft 140, in a direction generally parallel to the first axis A, may cause the rotary cutting bit 112 to rotate about the articulation axis B.

In some embodiments, the articulation shaft 140 is configured to prevent unintended movement of the rotary cutting bit 112, when the rotary cutting bit 112 is in use (e.g., being rotatably driven about the cutting axis C). For example, in use (e.g., during a minimally invasive arthroscopic surgery), the rotary cutting bit 112 may be disposed within the body of a patient and be rotatably driven about the cutting axis C to cut or shave away a bone spur. During said use, the rotary cutting bit 112 may be disposed at an articulated angle (e.g., as shown in FIG. 4), selected by a user (e.g., the surgeon), and it may be undesirable and/or dangerous should the angle of the rotary cutting bit 112 change unintentionally. As such, the articulation shaft 140 may be comprised of a generally rigid material (e.g., a metal, rigid plastic, metal alloy) to resist unintended movement of the rotary cutting bit 112. In some embodiments, the main shaft 142, elongated arm 144, and engagement member 146 are comprised of the same material. For example, the main shaft 142, elongated arm 144, and engagement member 146 may be comprised of a stainless steel (e.g., 316 stainless steel). In some embodiments, at least one of the main shaft 142, elongated arm 144, and engagement member 146 are comprised of a different material.

The translation of the articulation shaft 140 and corresponding rotation of the articulating head assembly 104 may be better understood with reference to FIGS. 7A-7B. In FIGS. 7A-7B there is shown side elevational views of the articulating head assembly 104 in a non-articulated position (e.g., as shown in FIG. 7A) and an articulated position (e.g., as shown in FIG. 7B). The elongated housing 102 is not shown in order to better illustrate the translation of the articulation shaft 140, however it will be understood that the elongated housing 102 may substantially enclose the articulation shaft 140 and may be positioned such that the distal end 110 of the elongated housing 102 abuts the lip 128 of the connecting member 124. As shown in FIG. 7A, the engagement member 146 of the articulation shaft 140 is engaged with the groove 150 of the cutting bit housing 114 and the articulating head assembly 104 is in the non-articulated position such that the first axis A and cutting axis C are generally aligned.

In the non-articulated position, the main shaft 142 of the articulation shaft 140 is a distance $d_1$ from the connecting member 124. The articulation shaft 140 may be translated in a direction parallel to the first axis A towards the connecting member 124 such that the articulating head assembly 104 is in an articulated position, as shown in FIG. 7B. In the articulated position, the main shaft 142 is a distance $d_2$ from the connecting member 124, where the distance $d_2$ is less than the distance $d_1$. In FIG. 7B, the articulating head assembly 104 is articulated such that it is at an angle θ relative to the first axis A. Put another way, the cutting axis C is at an angle θ relative to the first axis A, which may be about 15 degrees or about 30 degrees. In some embodiments, the angle θ is between about 0 degrees to about 15 degrees. In some embodiments, the angle θ is between about 15 degrees to about 30 degrees. In some embodiments, the angle θ is less than 30 degrees.

Figure 8:
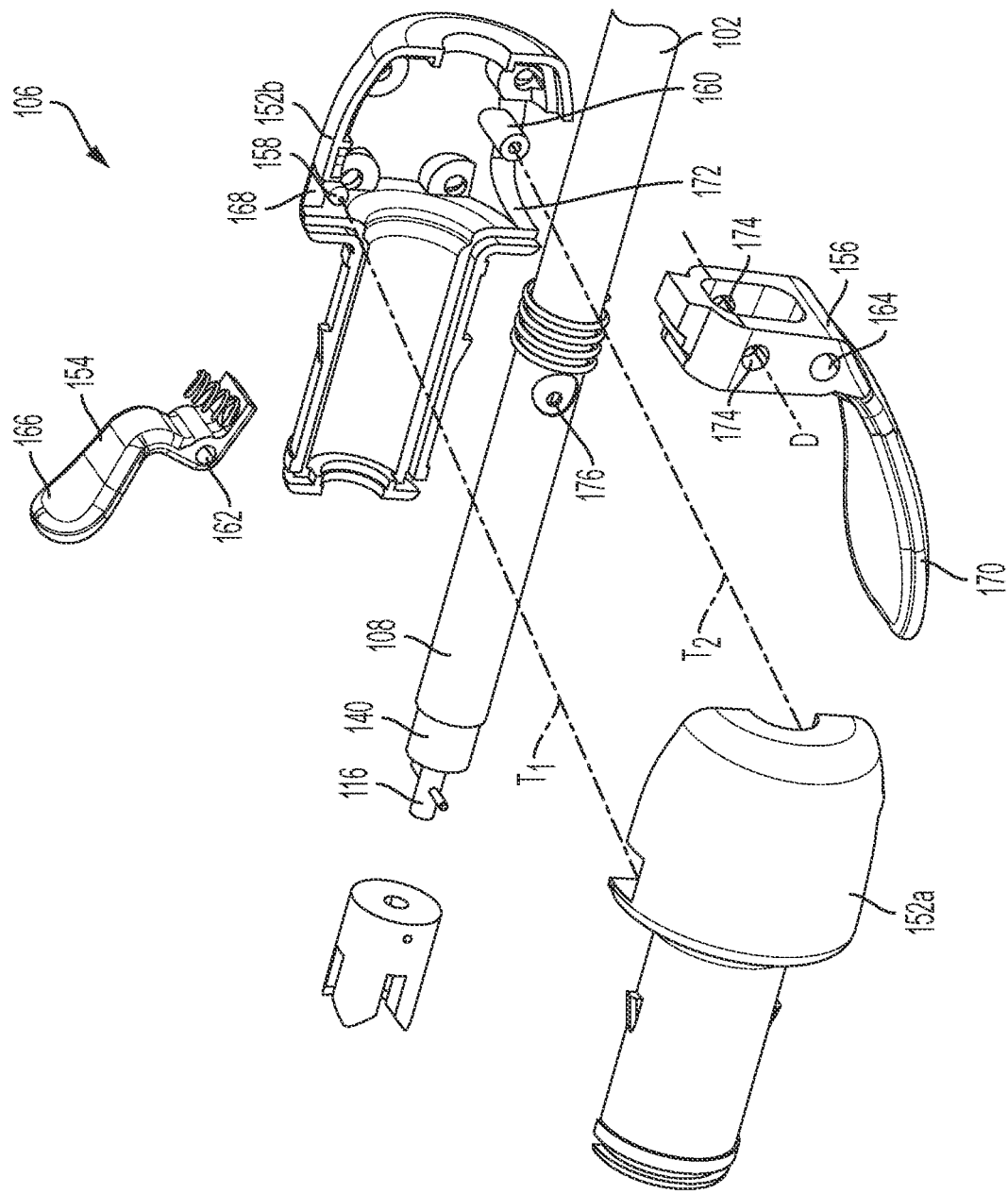
FIG. 8 is a partially exploded view of the controller assembly and proximal end of the articulating rotary cutting tool of FIG. 1.

In some embodiments, the angle θ of the articulating head assembly 104 may be a selectively controlled by the controller assembly 106. Referring to FIGS. 1 and 8, the controller assembly 106 may include a controller housing 152 formed of two housing sections 152a, 152b, a first trigger 154, and a second trigger 156 separate and distinct from the first trigger 154. The housing sections 152a and 152b may be coupled to the elongated housing 102 proximate the proximal end 108 of the elongated housing 102. In some embodiments, the housing sections 152a and 152b are fixedly coupled to the elongated housing 102 such that they are fixed relative to the elongated housing 102. In some embodiments, the housing sections 152a, 152b are comprised of a metal, metal alloy, plastic material, and/or a composite material. In some embodiments, the housing sections 152a, 152b are comprised of a synthetic polymer (e.g., Nylon 6/6, Nylon 12). In some embodiments, the housing sections 152a, 152b are comprised of a stainless steel. In some embodiments, the first trigger 154 and/or second trigger 156 are comprised of a metal, metal alloy, plastic material, and/or a composite material. In some embodiments, the first trigger 154 and/or second trigger 156 are comprised of a synthetic polymer (e.g., Nylon 6/6, Nylon 12). In some embodiments, the first trigger 154 and/or second trigger 156 are comprised of a stainless steel.

The first trigger 154 and second trigger 156 may be rotatably coupled to at least one of the housing sections 152a and 152b. For example, the housing section 152b may include a first protrusion 158 configured to rotatably couple the first trigger 154 to the housing section 152b and a second protrusion 160 configured to rotatably couple the second trigger 156 to the housing section 152b. In some embodiments, the housing section 152a may include protrusions similar to the first and second protrusions 158, 160 and positioned on the housing section 152a such that they are aligned with the first and second protrusions 158, 160. For example, the first protrusion 158 may extend along a first trigger axis $T_1$ and the second protrusion 160 may extend along a second trigger axis $T_2$ and the corresponding protrusions (not shown) extending from housing section 152a may extend along those same axes $T_1$, $T_2$, respectively. The first and second protrusions 158, 160 may be configured to rotatably couple each of the first and second triggers 154, 156 to the housing section 152b, respectively. It will be understood that the housing section 152a, having protrusions that are generally the same, is similarly configured to rotatably couple the first and second triggers 154, 156 to the housing section 152a and will not be described for sake of brevity. Put another way, it will be understood that the description of the coupling of the first and second triggers 154, 156 to housing section 152b is generally the same as for housing section 152a.

In some embodiments, the first trigger 154 may include an aperture 162 configured to receive at least a portion of the first protrusion 158 such that the first trigger 154 is coupled to the housing section 152b and is rotatable about the first trigger axis $T_1$. Similarly, the second trigger 156 may include an aperture 164 configured to receive at least a portion of the second protrusion 160 such that the second trigger 156 is coupled to the housing section 152b and is rotatable about the second trigger axis $T_2$. The first trigger 154 may include a user-engageable portion 166 configured to extend at least partially out of the controller housing 152. For example, the controller housing 152 may include an opening 168 proximate the first protrusion 158 that the user-engageable portion 166 extends through. Similarly, the second trigger 156 may include a user-engageable portion 170 configured to extend at least partially out of the controller housing 152 and the controller housing 152 may include an opening 172 proximate the second protrusion 160. As such, the user-engageable portion 170 of the second trigger 156 may extend through the opening 172.

In this manner, a user may apply a force to the user-engageable portions 166, 170 of the first and second triggers 154, 156 to selectively rotate the first and second triggers 154, 156 about the first and second trigger axes $T_1$, and $T_2$, respectively. In some embodiments, rotation of the second trigger 156 is configured to cause the articulating head assembly 104 to be rotated to an articulated position and rotation of the first trigger 154 is configured to cause the articulating head assembly 104 to be rotated toward the non-articulated position.

Figure 9:
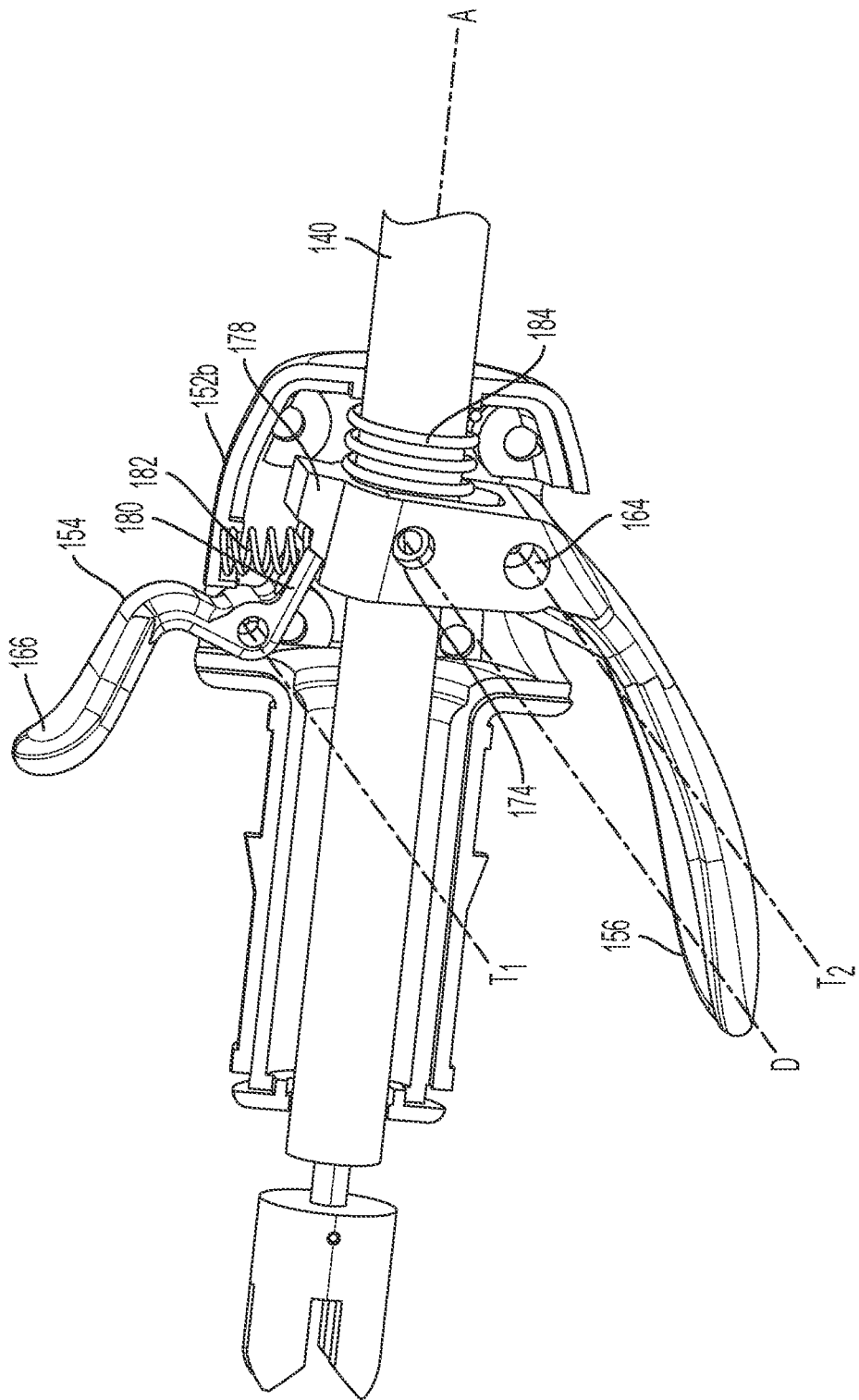
FIG. 9 is a perspective view of the controller assembly of FIG. 1 shown with half of the controller housing omitted.

Referring to FIGS. 8-9, the second trigger 156 may include at least one drive aperture 174 extending circumferentially around an axis D that is generally parallel with and spaced from the second trigger axis $T_2$. In some embodiments, the second trigger 156 includes two drive apertures 174, each extending circumferentially around the axis D and each having generally the same diameter. The drive apertures 174 may each be configured to receive a fastener (e.g., a screw, bolt, pin) to couple the second trigger 156 to the articulation shaft 140. For example, each drive aperture 174 is positioned on the second trigger 156 such that when the second trigger 156 is coupled to the second protrusion 160, each drive aperture 174 is aligned with a corresponding shaft aperture 176 extending through the articulation shaft 140. In this manner, a fastener may extend through each drive aperture 174 and the corresponding shaft aperture 176 such that the second trigger 156 is coupled to the articulation shaft 140.

In some embodiments, rotation of the second trigger 156 in a first direction (e.g., a clockwise direction) about the second trigger axis $T_2$ causes the articulating head assembly 104 (shown in FIG. 7B) to be rotated toward an articulated position. For example, as the second trigger 156 is rotated in a clockwise direction, the engagement of the second trigger 156 with the articulation shaft 140, via the drive apertures 174 and corresponding shaft apertures 176, causes the second trigger 156 to rotate relative to the articulation shaft 140 thereby causing the articulation shaft 140 to translate away from the proximal end 108 of the elongated housing 102. As such, the engagement of the articulation shaft 140 with the articulating head assembly 104, as discussed with reference to FIGS. 2 and 7B, may cause the articulating head assembly 104 to be rotated to an articulated position. In this manner, the second trigger 156 may be configured to cause the articulating head assembly 104 to be rotated to an articulated position, as shown, for example, in FIG. 7B.

Similarly, rotation of the second trigger 156 in a second direction (e.g., a counterclockwise direction), opposite the first direction, about the second trigger axis $T_2$ may cause the articulating head assembly 104 (shown in FIG. 7A) to be rotated toward a non-articulated position. For example, as the second trigger 156 is rotated in a counterclockwise direction, the engagement of the second trigger 156 with the articulation shaft 140, via the drive apertures 174 and corresponding shaft apertures 176, causes the second trigger 156 to rotate relative to the articulation shaft 140, thereby causing the articulation shaft 140 to translate toward the proximal end 108 of the elongated housing 102. As such, the engagement of the articulation shaft 140 with the articulating head assembly 104, as discussed with reference to FIGS. 2 and 7A, may cause the articulating head assembly 104 to be rotated toward the non-articulated position. In this manner, the second trigger 156 may be configured to cause the articulating head assembly 104 to be rotated toward the non-articulated position, as shown, for example, in FIG. 7A.

Figure 10:
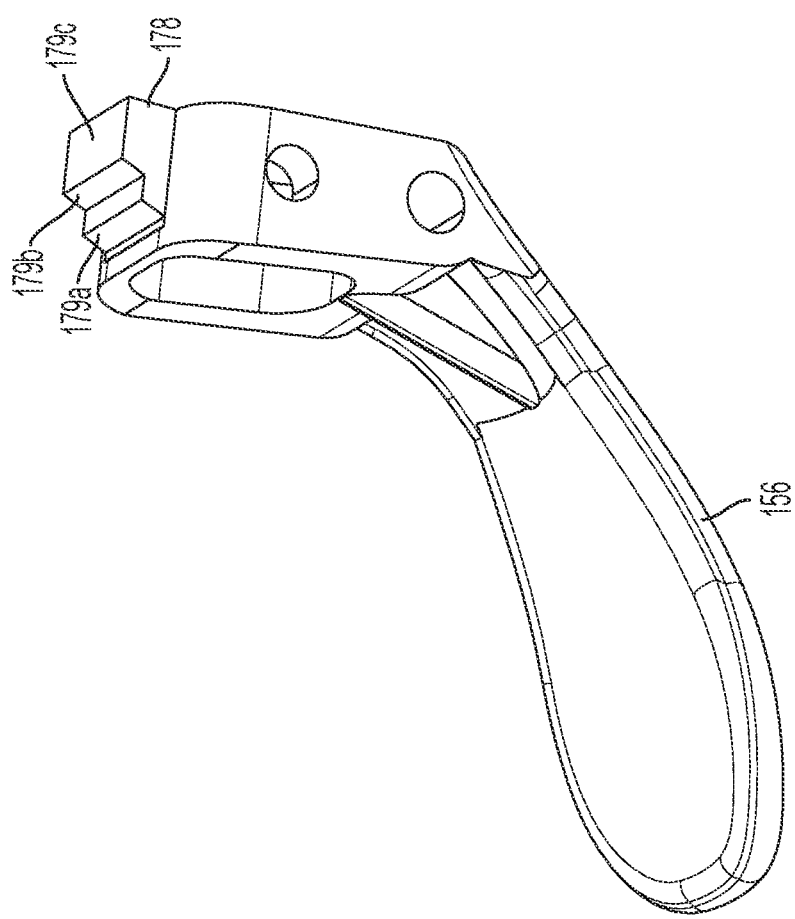
FIG. 10 is a perspective view of the second trigger of the controller assembly of FIG. 1.

Referring to FIGS. 7B, and 9-10, the second trigger 156 and first trigger 154 may releasably retain the articulating head assembly 104 (shown in FIG. 7B) in one or more articulated positions. In some embodiments, the second trigger 156 includes a stepped structure 178 defining one or more stepped surfaces each configured to engage an arm 180 of the first trigger 154. The stepped structure 178 includes two stepped surfaces 179*a*-179*b* that each correspond to a different predetermined articulated position of the articulating head assembly 104. In some embodiments, the stepped surface 179*a* corresponds to a first articulated position in which the articulating head assembly 104 is at an angle θ of about 30 degrees relative to the first axis A (see FIG. 7B for reference). Similarly, the stepped surface 179*b* may correspond to a second articulated position, in which the articulating head assembly 104 is at an angle θ of about 15 degrees relative to the first axis A (see FIG. 7B for reference). In some embodiments, the arm 180 of the first trigger 154 engages a stepped surface 179*a*-179*b* when the articulating head assembly 104 is in the first or second articulated position. In some embodiments, the arm 180 rests on the top planar surface 179*c* of the stepped structure 178 when the articulating head assembly 104 is in the non-articulated position (e.g., when angle θ is zero degrees). In some embodiments, the arm 180 is biased towards engagement with the stepped structure 178 by a biasing member 182. The biasing member 182 may be a compression spring or any other biasing member known to those skilled in the art.

When the articulating head assembly 104 is in the first or second articulated positions, the arm 180 of the first trigger 154 may abut the corresponding stepped surface 179*a*, 179*b* such that the second trigger 156 is prevented from rotating about the second trigger axis $T_2$ in at least one direction (e.g., counterclockwise). For example, when the arm 180 abuts one of the stepped surfaces 179*a*, 179*b*, the first trigger 154 prevents, or at least resists, rotation of the second trigger 156 in a counterclockwise direction. As discussed above, the second trigger 156 is coupled to the articulation shaft 140, which is coupled to the articulating head assembly 104, such that rotation of the second trigger 156, translation of the articulation shaft 140, and rotation of the articulating head assembly 104 each correspond to one another. Put another way, rotation of the second trigger 156 causes translation of the articulation shaft 140, which causes the articulating head assembly 104 to rotate, and vice versa. As such, the first trigger 154, when the arm 180 is engaged with one of the stepped surfaces 179*a*, 179*b*, may resist or prevent translation of the articulation shaft 140 in at least one direction (e.g., toward the proximal end 108 of the elongated housing 102), thereby also preventing rotation of the articulating head assembly 104 in at least one direction. In this manner, the first trigger 154 may provide additional stability to the articulating head assembly 104 when the rotary cutting bit 112 is cutting or drilling to prevent, or at least resist, unintended rotation of the rotary cutting bit 112 about the articulation axis B.

In some embodiments, the first trigger 154 may be configured to allow rotation of the second trigger 156 in at least one direction (e.g., clockwise) while the arm 180 of the first trigger 154 is engaged with the stepped structure 178 of the second trigger 156. For example, when the arm 180 abuts stepped surface 179*b*, the second trigger 156 may be freely rotated in a clockwise direction such that the arm 180 disengages the stepped surface 179*b* and engages the stepped surface 179*a*. In this manner, the first trigger 154 may allow a user to freely rotate the articulating head assembly 104 from the second articulated position to the first articulated position.

In some embodiments, a user may manually rotate the first trigger 154 such that the articulating head assembly 104 is automatically rotated toward the non-articulated position (shown in FIG. 7A). For example, a user may apply a force to the user-engageable portion 166 of the first trigger 154 to cause the first trigger 154 to rotate counter-clockwise about the first trigger axis $T_1$. In this manner, the arm 180 may be disengaged from the stepped structure 178 of the second trigger 156, thereby allowing the second trigger 156 to be rotated in a counterclockwise direction. In some embodiments, there may be a second biasing member 184 disposed within the controller housing 152 and configured to bias the second trigger 156 toward a first position in which the articulating head assembly 104 is in the non-articulated position. As such, when a user manually rotates the first trigger 154 in a counterclockwise direction such that the arm 180 is not engaged with the stepped structure 178, the second biasing member 184 causes the second trigger 156 to be rotated to the first position. As such, the second biasing member 184 biases the articulation shaft 140 toward the proximal end 108 of the elongated housing 102, thereby also biasing the articulating head assembly 104 toward the non-articulated position. This may allow a user to selectively rotate the articulating head assembly 104 between any one of the articulated positions and the non-articulated position.

In some embodiments, the articulating rotary cutting tool 100 may be configured to be used in surgical procedures where articulation of the head assembly 104 is not required and/or beneficial. Put another way, in certain surgical operating environment it may be beneficial to provide a rotary cutting tool similar to the articulating rotary cutting tool 100 except that the articulating head assembly 104 is not rotatable about the articulation axis B. For example, in oral and maxillofacial surgical procedures, articulation of the articulating head assembly 104 may not be required and/or it may be beneficial to provide the articulating head assembly 104 at a fixed angle θ to thereby increase the stability of the rotary cutting bit 112 when drilling or cutting. The articulating head assembly 104 may be fixedly oriented in the non-articulated position (e.g., where angle θ is 0 degrees) or any articulated position (e.g., where angle θ is greater than 0 degrees and/or up to about 30 degrees). In such embodiments, the constant velocity joint formed between the rotary cutting bit 112 and rotary socket 118 may function generally the same as described above. Put another way, the cutting bit housing 114 may be fixedly coupled to the connecting member 124 such that the cutting bit housing 114 is fixed at a predetermined angle θ. As such, the rotary cutting bit 112 may be coupled to the cutting bit housing 114, as described above, and the multi-faceted ball 122 of the rotary cutting bit 112 may be received within the receiving area 120 of the rotary socket 118 such that rotation of the rotary socket 118 at a rotational velocity causes the rotary cutting bit 112 to be rotated at generally the same rotational velocity.

In some embodiments, the articulating rotary cutting tool 100 may be configured to be used with an oscillating saw mechanism (not shown). For example, the rotary cutting bit 112 may be replaced by a saw, blade, or rasp that oscillates generally along the cutting axis C. The saw may be articulable about the articulation axis B and the articulating rotary cutting tool 100 may include an oscillation mechanism (not shown) configured to convert the rotational motion of the drive shaft 116 to an oscillating linear motion along the cutting axis C. In some embodiments the oscillation mechanism is positioned within the elongated housing 102 and located proximate the distal end 110. In other embodiments, the oscillation mechanism is positioned within the cutting bit housing 114.

Figure 11:
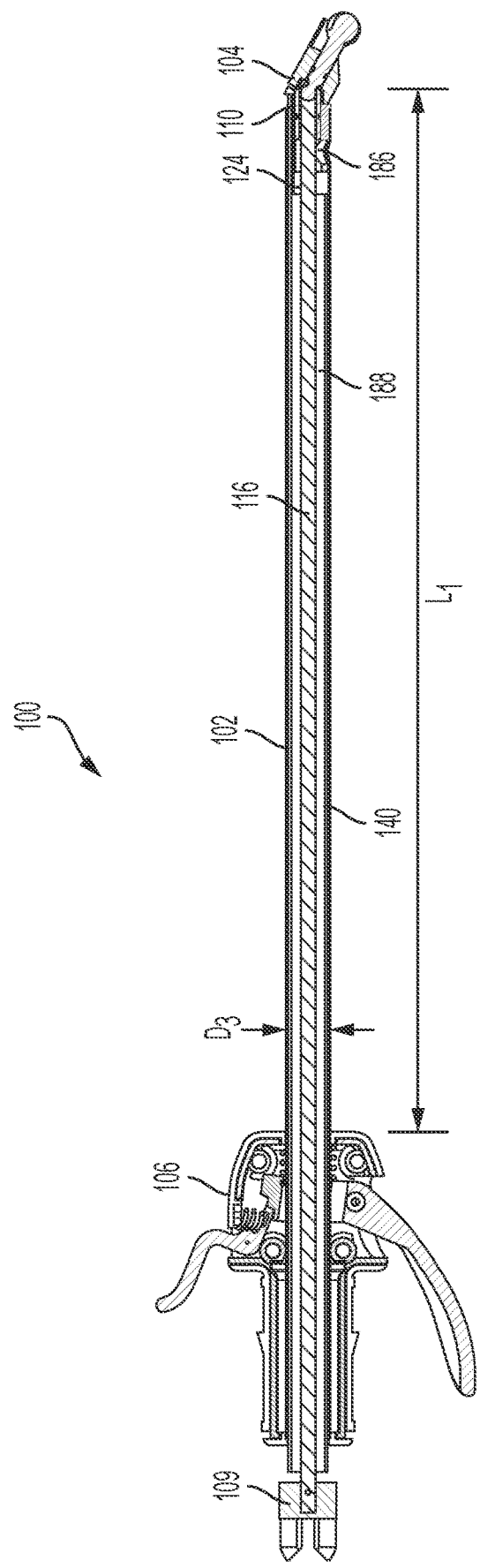
FIG. 11 is a side cross-sectional elevational view of the articulating rotary cutting tool of FIG. 1.

Referring to FIGS. 2 and 11, the articulating rotary cutting tool 100 may include a fluid suction intake 186 configured to aspirate fluid proximate the articulating head assembly 104. In some embodiments, the drive means coupled to the drive interface 109 may include a motor to drive the drive shaft 116 and concurrently aspirate fluid through the fluid suction intake 186. For example, the drive means may include means for creating a vacuum, suction, and/or aspiration. In some embodiments, the fluid suction intake 186 is formed on the elongated housing 102 and acts as an opening through which fluid may pass. In some embodiments, there is a channel 188 formed between the drive shaft 116, articulation shaft 140, and the connecting member 124 that is in fluid communication with the fluid suction intake 186 such that fluid may be flowed through the fluid suction intake 186 and through the channel 188. In some embodiments, there is a fluid receiving means in fluid communication with the channel 188 such that the aspirated fluid may be removed from the channel 188 and the articulating rotary cutting tool 100. In some embodiments, there may be a fluidly sealed partition (not shown) surrounding the drive shaft 116 such that the aspirated fluid does not contact the drive shaft 116. In other embodiments, the drive shaft 116 may include elements to aid the aspiration of the fluid through the fluid suction intake 186, such as, but not limited to, grooves or projections.

In some embodiments, the fluid being aspirated through the fluid suction intake 186 may be prevented from contacting the constant velocity joint formed between the rotary cutting bit 112 and rotary socket 118 by the connecting member 124 and/or receiving area 120 of the rotary socket 118 as described above with reference to FIG. 2. In other embodiments, the articulating rotary cutting tool 100 may not include a fluid suction intake 186. For example, in non-arthroscopic applications (e.g., robotic surgical applications, endoscopic spinal surgical applications) aspiration of fluid may not be required. In such applications, the fluid suction intake 186 may not be included such that the elongated housing 102 does not include the opening for the fluid suction intake 186.

In some embodiments, the articulating rotary cutting tool 100 has a length $L_1$ as measured from a distal end of the controller assembly 106 to a distal end 110 of the elongated housing 102 and the elongated housing 102 has a diameter $D_3$. In some embodiments, the length $L_1$ is between about 200 millimeters to about 250 millimeters. In some embodiments, the length $L_1$ is at least 200 millimeters. In some embodiments, the length $L_1$ is less than or equal to 250 millimeters. In some embodiments, the length $L_1$ is at least 200 millimeters. In some embodiments, the length $L_1$ is less than or equal to 225 millimeters. In some embodiments, the length $L_1$ is about 212 millimeters. The diameter $D_3$ of the elongated housing 102 may be between about 5 millimeters to about 10 millimeters. In some embodiments, the diameter $D_3$ of the elongated housing 102 is greater than 5 millimeters. In some embodiments, the diameter $D_3$ is less than or equal to about 10 millimeters. In some embodiments, the diameter $D_3$ is less than or equal to about 8 millimeters. In some embodiments, the diameter $D_3$ is about 7 millimeters. It will be understood that the length $L_1$ and diameter $D_3$ may correspond to the intended surgical use and may therefore be changed depending on the intended surgical use. For example, the articulating rotary cutting tool 100 shown in FIG. 11 configured for a spinal surgical use may have a length and/or diameter that is different from what is shown in FIG. 11.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A rotary cutting tool comprising:
   an elongated housing having a proximal end and a distal end, the elongated housing extending circumferentially around a first axis;
   a drive shaft disposed within the elongated housing and extending along the first axis between the proximal end and the distal end, the drive shaft being rotatable about the first axis;
   a rotary cutting bit including a multi-faceted ball that forms a constant velocity joint with the drive shaft, the rotary cutting bit being rotatable relative to the drive shaft where the constant velocity joint is formed about an articulation axis that intersects the first axis;
   a cutting bit housing coupled to the distal end of the elongated housing and the rotary cutting bit, the cutting bit housing being rotatable relative to the drive shaft and constraining rotation of the rotary cutting bit about the articulation axis between a non-articulated position and one or more articulated positions; and
   an articulation shaft disposed between the elongated housing and drive shaft and including an elongated arm protruding distally from the elongated housing and an engagement member fixedly coupled to the elongated arm, the engagement member having a concave surface and an opposed convex surface, the engagement member coupled to the cutting bit housing.

2. The rotary cutting tool of claim 1 further comprising:
   a controller assembly coupled to the proximal end of the elongated housing and configured to cause the rotary cutting bit and cutting bit housing to selectively rotate relative to the elongated housing between the non-articulated position and the one or more articulated positions.

3. The rotary cutting tool of claim 2, wherein the controller assembly is coupled to the articulation shaft and configured to cause the articulation shaft to translate relative to the elongated housing, and wherein translation of the articulation shaft relative to the elongated housing causes the rotary cutting bit and cutting bit housing to rotate relative to the elongated housing about the articulation axis.

4. The rotary cutting tool of claim 3, wherein the controller assembly includes a first trigger and a second trigger, the second trigger configured to cause the articulation shaft to translate relative to the elongated housing and the first trigger configured to releasably lock a position of the articulation shaft relative to the elongated housing.

5. The rotary cutting tool of claim 4, wherein the first trigger includes an arm configured to abut a stepped structure of the second trigger such that rotation of the second trigger in at least one direction is prevented by the arm of the first trigger.

6. The rotary cutting tool of claim 5, wherein the stepped structure includes one or more stepped surfaces that each correspond to a different articulated position of the one or more articulated positions.

7. The rotary cutting tool of claim 3, wherein the articulation shaft, the engagement member and the elongated arm are integrally formed and are comprised of a generally rigid material.

8. The rotary cutting tool of claim 1, wherein the drive shaft includes a rotary socket configured to receive the multi-faceted ball of the rotary cutting bit, the multi-faceted ball and rotary socket forming the constant velocity joint.

9. The rotary cutting tool of claim 8, wherein the rotary socket is rotatably fixed to the drive shaft such that rotation of the drive shaft about the first axis causes the rotary socket to rotate about the first axis,
wherein the rotary socket defines a receiving area for receiving the multi-faceted ball, and
wherein the receiving area has a generally hexagonal shape and the multi-faceted ball is a hex-ball.

10. The rotary cutting tool of claim 8, wherein the rotary socket includes a groove extending circumferentially around the rotary socket, and the elongated housing is configured to receive two fasteners such that the two fasteners are at least partially received within the groove to prevent translation of the rotary socket about the first axis.

11. The rotary cutting tool of claim 1, wherein the rotary cutting bit includes a groove extending circumferentially around a central shaft of the rotary cutting bit, the groove configured to receive a fastener to prevent the rotary cutting bit from translating relative to an intended cutting axis.

12. The rotary cutting tool of claim 1, wherein the multi-faceted ball of the rotary cutting bit is directly connected to the drive shaft where the articulation axis intersects the first axis, and wherein the drive shaft has a single axis of rotation.

13. The rotary cutting tool of claim 1, wherein the rotary cutting bit includes a cutting head extending along a cutting axis and having a proximal end coupled to a central shaft, the cutting head having a plurality of resecting surfaces each contacting one another at a distal end of the cutting head at a point on the cutting axis.

14. The rotary cutting tool of claim 1, wherein the rotary cutting bit is rotatable about the articulation axis by up to 30 degrees.

15. The rotary cutting tool of claim 1, wherein the elongated housing includes a fluid suction intake configured to aspirate fluid proximate to the cutting bit housing, the fluid suction intake being in fluid communication with a channel interior to the elongated housing.

16. The rotary cutting tool of claim 1, wherein the cutting bit housing has a proximal end including a first side portion and a second side portion extending from the first side portion at an oblique angle, the oblique angle being substantially equal to a maximum articulation angle of the cutting bit relative to the drive shaft, and
wherein, in at least one of the articulated positions, the second side portion of the cutting bit housing at least partially abuts the distal end of the elongated housing.

17. The rotary cutting tool of claim 16, wherein the cutting bit housing includes a distal end having an upper distal portion and a lower distal portion, the upper distal portion defining a shield partially overlapping a cutting head of the cutting bit in a longitudinal direction, the lower distal portion extending downwardly from the upper distal portion at an oblique angle.

18. The rotary cutting tool of claim 16, wherein the first side portion of the proximal end prevents the cutting bit from rotating in a first direction when in the non-articulated position, and
wherein the second side portion of the proximal end prevents the cutting bit from rotating in a second direction opposite the first direction when in at least one of the articulated positions.

19. The rotary cutting tool of claim 1, wherein the cutting bit extends distally past a distal end of the cutting bit housing.

20. The rotary cutting tool of claim 1, wherein the articulation shaft includes a main shaft portion that extends from the proximal end of the elongated housing to the distal end thereof, the drive shaft being enclosed within the main shaft.

21. The rotary cutting tool of claim 20, wherein the main shaft extends circumferentially around the first axis and the elongated arm protrudes distally from a distal end of the main shaft, and
wherein the elongated arm extends partially around the first axis.

22. The rotary cutting tool of claim 1, wherein the cutting bit housing includes a groove that extends along an outer surface of the cutting bit housing and the engagement member is coupled to the groove.

23. The rotary cutting tool of claim 1, wherein the engagement member has a curved T-shape.

24. An arthroscopic rotary cutting tool comprising:
an elongated housing having a proximal end and a distal end, the elongated housing extending circumferentially around a first axis;
a drive shaft disposed within the elongated housing and extending along the first axis between the proximal end and the distal end, the drive shaft being rotatable about the first axis, the drive shaft including a rotary socket;
a rotary cutting bit including a multi-faceted ball that forms a constant velocity joint with the rotary socket of the drive shaft, the rotary cutting bit being rotatable relative to the drive shaft where the constant velocity joint is formed about an articulation axis that intersects the first axis;
a cutting bit housing having a groove extending along an outer surface of the cutting bit housing and coupled to the distal end of the elongated housing and the rotary cutting bit, the cutting bit housing being rotatable relative to the drive shaft and constraining rotation of the rotary cutting bit about the articulation axis between a non-articulated position and one or more articulated positions;
a controller assembly coupled to the proximal end of the elongated housing and configured to cause the rotary cutting bit and cutting bit housing to selectively rotate relative to the elongated housing between the non-articulated position and the one or more articulated positions; and an articulation shaft disposed between the elongated housing and including an elongated arm protruding distally from the elongated housing and an engagement member fixedly coupled to the elongated arm, the engagement member having a concave surface and an opposed convex surface, the engagement member received within the groove in the cutting bit housing, and the articulation shaft, elongated arm and engagement member being translatable in the same direction with one another, wherein the controller assembly is coupled to the articulation shaft and configured to cause the articulation shaft to translate relative to the elongated housing, and wherein translation of the articulation shaft relative to the elongated housing causes the rotary cutting bit and cutting bit housing to rotate relative to the elongated housing about an articulation axis.

25. The arthroscopic rotary cutting tool of claim 24, wherein the controller assembly includes a first trigger and a second trigger, the second trigger configured to cause the articulation shaft to translate relative to the elongated housing and the first trigger configured to releasably lock a position of the articulation shaft relative to the elongated housing.

26. The arthroscopic rotary cutting tool of claim 25, wherein the first trigger includes an arm configured to abut a stepped structure of the second trigger such that rotation of the second trigger in at least one direction is prevented by the arm of the first trigger.

27. The arthroscopic rotary cutting tool of claim 26, wherein the stepped structure includes one or more stepped surfaces that each correspond to a different articulated position of the one or more articulated positions.

28. The arthroscopic rotary cutting tool of claim 24, wherein the rotary socket is rotatably fixed to the drive shaft such that rotation of the drive shaft about the first axis causes the rotary socket to rotate about the first axis, wherein the rotary socket defines a receiving area for receiving the multi-faceted ball, and wherein the receiving area has a generally hexagonal shape and the multi-faceted ball is a hex-ball.

29. The arthroscopic rotary cutting tool of claim 24, wherein the rotary socket includes a groove extending circumferentially around the rotary socket, and the elongated housing is configured to receive two fasteners such that the two fasteners are at least partially received within the groove to prevent translation of the rotary socket about the first axis.

* * * * *